Figure 1A:
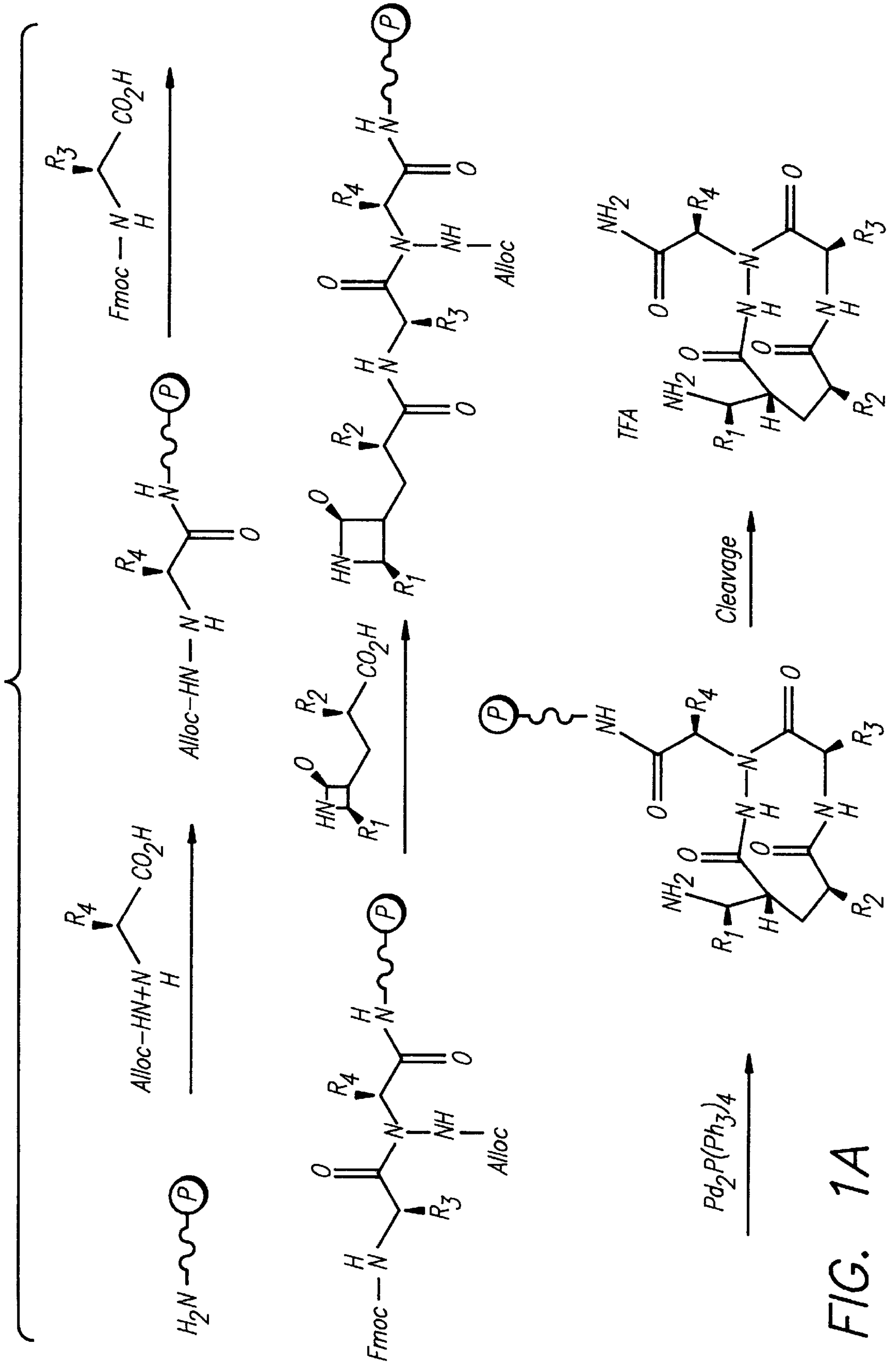

US005846933A

United States Patent [19]

Korngold et al.

[11] Patent Number: 5,846,933

[45] Date of Patent: Dec. 8, 1998

[54] CD-4 DERIVED PEPTIDES THAT INHIBIT IMMUNE RESPONSES

[76] Inventors: Robert Korngold, 101 Dalton Ter., Cherry Hill, N.J. 08003; Ziwei Huang, 505C S. Tenth St., Philadelphia, Pa. 19147

[21] Appl. No.: 672,610

[22] Filed: Jun. 28, 1996

[51] Int. Cl.$^{6}$ ...................................................... A61K 38/00

[52] U.S. Cl. ...................... 514/11; 424/185.1; 424/278.1; 514/2; 514/9; 514/903; 530/317

[58] Field of Search .............................. 424/185.1, 278.1; 514/11, 2, 9, 903; 530/317

[56] References Cited

U.S. PATENT DOCUMENTS 4,963,657 10/1990 Pixley .
5,109,123 4/1992 Reinherz et al. .

FOREIGN PATENT DOCUMENTS

94/11014 5/1994 WIPO .

OTHER PUBLICATIONS

Satoh et al *BBRC* 224 pp. 438–443, 1996.
Osband et al *Immunology Today* 11(6) pp. 193–195, 1990.
R. Mehta et al., “Synthetic Peptides of Human CD4 Enhance Binding of Immunoglobulins to Monocyte/Macrophage Cells,” *Cellular Immunology*, 156:146–154 (1994).
M. Goodman et al., “Tropochemical Design of Bioactive Peptides and Peptidomimetics,” 18(10–11):1375–1393 (1992).
Acha–Orbea, H., et al., 1988, Cell 54:263–273.
Hafler, D.A., et al., 1988, J. Immunol. 141:131–138.
Jameson, B.A., et al., 1994, Nature 368:744–746.
Lindsey, J.W., et al., 1994, Animals of Neurology 36:183–189.
Racadot, E. et al., 1993, J. Autoimmunity 6:771–786.
Steinman, L., et al., 1981, Proc. Natl. Acad. Sci. USA 78:7111–7114.
Waldor, M.K., et al., 1985, Science 227:415–17.
Wraith, D.C., et al., 1989, Cell 59:247–255.
Zhang, X., et al., 1996, Nature Biotechnology, 14:472–475.

*Primary Examiner*—Paula K. Hutzel
*Assistant Examiner*—Heather A. Bakalyar
*Attorney, Agent, or Firm*—Pennie & Edmonds LLP

[57] ABSTRACT

The application concerns a method of identifying compounds that can be used to inhibit undesired human CD4$^{+}$T cell immune responses by identifying compounds that block the interaction of CD4 and MHC, class II, gene products and a method of treatment which comprises administering such an identified compound. The compounds that inhibit undesired human CD4$^{+}$T cell immune responses can be used to treat disease such as multiple sclerosis and to prevent graft rejection and graft versus host disease. More specifically, the application concerns compounds having molecular weights between about 1400 and 400 that mimic three portions of the human CD4 lymphocyte cell surface antigen. The portions are residues 29–35, the C–C' loop of the D1 domain; residues 317–323, the C–C' loop of the D4 domain; and residues 346–353, the CDR3 or FG ridge of the D4 domain of the CD4 molecule. Specific examples of such compounds include cyclic peptides and peptidomimetic.

11 Claims, 4 Drawing Sheets

CD-4 DERIVED PEPTIDES THAT INHIBIT IMMUNE RESPONSES

This application is a continuation-in-part of U.S. provisional applications Ser. No. 60/000,710, filed Jun. 29, 1995, and Ser. No. 60/004,034, filed Sept. 20, 1995, which are, each, hereby incorporated by reference in their entirety.

1. FIELD OF THE INVENTION

The present invention relates to the suppression of immune responses caused by the activation of T cells. More particularly, it concerns compounds that mimic the surface of CD4 protein molecules, thereby interfering with the interaction of the CD4 and MHC, class II, gene products and methods of identifying and using such compounds to suppress undesired immune responses.

2. BACKGROUND OF THE INVENTION

A T cell is a type of lymphocyte, or "white blood cell", that mediates the cellular immune response to foreign macromolecules, termed antigens. While T cells are necessary for normal mammalian immune responses, in some instances it is desirable to inhibit their activation: for example, in some autoimmune diseases, the T cells of a subject respond to "self-antigens", i.e., macromolecules produced by the subject, rather than foreign-made macromolecules, and damage the cells and tissues of the subject.

Autoimmune T cell responses are found in subjects having systemic lupus erythematosus (SLE), rheumatoid arthritis (RA), insulin-dependent diabetes and multiple sclerosis (MS) and contribute to the pathophysiology of each.

T cells also cause graft rejection and graft versus host disease (GVHD). Graft rejection is caused by an immune response against the transplanted tissues (the graft), which are recognized as "foreign" by T cells of the recipient (host). Graft versus host disease is caused by engrafted T cells, which recognize host-made macromolecules as "foreign."

2.1. Role of CD4 in T Cell Activation

The CD4 molecule, a member of the immunoglobulin super-family, is a glycoprotein expressed on the surface of helper T cells, White, R. H. H., et al., 1978, J.Exp. Med. 148:664–73, which are one of the two major types of T cells. Helper T cells recognize antigens only when the antigens are associated with the class II products of the Major Histocompatibility Complex (class II MHC). CD4 and the T cell antigen receptor are involved in a signal transduction pathway whereby the presence of an antigen leads to the activation of an antigen-specific helper T cell. CD4 is involved in the antigen-free, intra-thymic selection of the T cell repertoire. Teh, H. S., et al., 1991, Nature 349:241–43.

The CD4 molecule has two critical functions. First, as a co-receptor with the T cell antigen receptor, CD4 binds to a non-polymorphic region of the β-chain of the class II MHC molecule on the antigen-presenting cell. Doyle, C. & Strominger, J. L., 1987, Nature 330:256–59; Gay, D., et al., 1987, Nature 328:626–29; Konig, R., et al., 1995, Nature 365:796–98. CD4 can potentiate the T cell response as much as 300 fold above the level obtained without CD4. Janeway, C. A., 1991, Seminars in Immunology 3:153–160. Second, extensive evidence suggests that CD4 is a signal transduction molecule. Studies have shown: that the cytoplasmic tail of CD4 is associated with the tyrosine kinase $p56^{lck}$, Veillette, A., et al., 1988, Cell 55:301–08; Barber, E. K., et al. 1989, Proc. Natl. Acad. Sci. 86:3277–81; Turner, J. M., et al., 1990, Cell 60:755–65; that stimulation of CD4 with an anti-CD4 monoclonal antibody increases the activity of the $p56^{lck}$ kinase, Veillette, A., et al., 1989, Nature 335:257–9; and that cross-linking of CD4 and the T cell antigen receptor enhances both T cell antigen receptor-mediated tyrosine phosphorylation, June, C. H., et al., 1990, J. Immunol. 144:1591, and lymphokine production, Anderson, P., et al., 1987, J. Immunol. 139:678–82; Emmrich, F., et al., 1987, Eur. J. Immunol. 17:529–34. These studies imply that CD4 molecules interact with the other cell-surface molecules of the T cell antigen receptor complex during the transduction of signals leading to the activation of the cell, Miceli, M. C. & Parnes, J.R., 1993, Adv. Immunol. 53:59–122: e.g., with the T cell antigen receptor/CD3 complex, Saizawa, K., et al., 1987, Nature 328:260–63; Rivas, A., 1988, J.Immunol. 140:2912–18; and with the CD45 tyrosine phosphatase, Dianzani, U., et al., 1990 Eur. J. Immunol. 20:2249–57. There have been a CD4—CD4 interactions observed between solubilized CD4 proteins, Davis, S.J., et al., 1990, J.Biol.Chem. 265:10410.

Recently, it has been suggested that oligomerization of CD4 on the cell surface may be required for stable binding to class II MHC and T-cell activation. Sakihama, T., et al., 1995, Proc. Natl. Acad. Sci. 92:6444. If there is an interaction between membrane bound CD4 proteins, molecular modeling data is consistent with the participation in the interaction of the CDR3 and C–C' loops of the D1 domains of the CD4 proteins, Langedijik, J. P. M., et al., 1993, J.Biol.Chem. 268:16875–78. The external domains (D1–D4) of the CD4 molecule are involved in these protein-protein interactions.

The studies of the interaction of CD4 and MHC, class II, gene products have been performed to determine whether mutations at selected residues of CD4 block the binding of CD4 transfected cells and MHC, class II, bearing cells. These studies suggest that the interaction involves large areas of the CD4 molecule, in particular most of the lateral surfaces of the D1 domain and the upper part of the D2 domain. Clayton, L.K. et al., 1989, Nature 339:548–51; Moebius, U. et al., 1992, Proc. Natl. Acad. Sci. 89:12008–12; Moebius, U., et al., 1993, Proc. Natl. Acad. Sci. 90:8259–63.

The apposition of the CD4 tyrosine kinase $p56^{lck}$, the T cell antigen receptor tyrosine kinase $p59^{fyn}$, and the CD45 tyrosine phosphatase, then leads to the signals that activate the T cell. Veillette, A., et al., 1988, Cell 55:301–08; Barber, E. K., et al. 1989, Proc. Natl. Acad. Sci. 86:3277–81.

2.2. Multiple Sclerosis Is Mediated by $CD4^{+}$T cells

Pathologically, the lesions of MS consist of perivascular inflammatory cuffs in the white matter of the central nervous system. These contain activated and non-activated lymphocytes, plasma cells, monocytes, and macrophages. The majority of the small lymphocytes found in early lesions are of the helper-type, $CD4^{+}$T cell subset. Raine, C. S., et al., 1988, J. Neuroimmunol. 20:189–201; Raine, C. S., 1991, Neuropath. Appl. Neurobiol. 17:265–274.

An animal model useful for the study of the treatment of human MS is experimental allergic encephalomyelitis (EAE). EAE is an experimentally induced disease that shares many of the same clinical and pathological symptoms of MS, Martin, R., et al., 1992, Ann. Rev. Immunol. 10:153–187; Hafler, D. A., et al., 1989, Immunology Today 10:104–107. Several studies in rodents have shown that, similar to MS, $CD4^{+}$T cells participate in the pathophysiology of EAE, Traugott, U., et al., 1985, Cellular Immunology 91:240–254; Ben-Nun, A., et al., 1981, Eur. J. Immunol. 11:195–199; Pettineli, R. B., et al., 1981, J. Immunol. 127:1420–1423. EAE can be induced in certain strains of mice by immunization with myelin in an adjuvant. The immunization activates $CD4^+$T cells specific for myelin basic protein (MBP) and proteolipid (PLP), Bernard, C. C. A., et al., 1975, J. Immunol. 114:1537–1540; Chou, C.H., et al., 1983, J. Immunol. 130:2183–2186; Kurchroo, V.K., et al., 1992, J. Immunol. 148:3776–3782. The activated T cells enter the central nervous system and their local action causes both the anatomic pathology and clinical signs, e.g., ascending hind limb paresis leading to paralysis, of the disease.

Since autoreactive $CD4^+$T cells have an important role in mediating the pathogenesis of MS, one approach to treating the disease is inhibiting the activation of autoreactive, $CD4^+$T cells. One can use for this purpose monoclonal antibodies (mAbs) to class II MHC, Steinman, L., et al., 1993, Proc. Natl. Acad. Sci. USA 78:7111–7114, or to the T cell antigen receptor, Acha-Orbea, H., et al., 1988, Cell 54:263–273. One can also competitively inhibit antigen binding to class II MHC with non-immunogenic peptides, Wraith, D. C., et al., 1989, Cell 59:247–255.

Anti-CD4 mAbs have also been shown to inhibit the development of the disease in EAE, Waldor, M. K., et al., 1985, Science 227:415–17, and several human clinical trials are currently in progress to test this approach in MS, Hafler, D. A., et al., 1988, J. Immunol. 141:131–138; Racadot, E. et al., 1993, J. Autoimmunity 6:771–786; Lindsly, J. W., et al., 1994, Annals of Neurology 36:183–189.

2.3. Inhibition of Immune Responses By CD4-Derived Peptides

Synthetic peptides that mimic the surface of the CD4 molecule have been used to block the function of the CD4 protein. For example, peptides, the sequence of which is derived from the sequence of the CDR3 loop of the mouse CD4 molecule have been shown to inhibit T cell activation, in vitro, and also to ameliorate murine EAE, Jameson, B.A., et al., 1994, Nature 368:744–746. These experiments have established that: (i) treatment using a CDR3-derived peptide inhibits the autoreactive T cells but not normal immune responses; (ii) treatment using a CDR3-derived peptide does not cause pan-$CD4^+$T cell-depletion, a peptide specific immune response, or toxic side effects, so that the chronic use of such peptides is feasible; and (iii) treatment using a CD4-derived peptide inhibits secondary T cell responses, which would likely be involved in a clinical relapse of disease, Jameson, B.A., et al., 1994, Nature 368: 744–746; WO094/11014 to Jameson, B.A., et al. The peptides used in the Jameson studies contained a 9-amino acid sequence derived from residues 86–94 of CD4 and an amino acid linker to cyclize the peptide.

WO094/11014 by B.A. Jameson et al., published May 26, 1994, discloses that peptides having sequences derived from the sequence of residues 17–22, 117–128, 130–138, and 158–171 of CD4, and subregions thereof, may also be used to modulate an immune response. Additional peptides are disclosed in U.S. Pat. application Ser. No. 08/368,280 by R. Korngold and B.A. Jameson, filed Jan. 3, 1995.

Zhang, X., et al., 1996, Nature Biotechnology, 14:472–475 discloses a peptide having a molecular weight of about 1500 daltons and containing residues 82–89 of CD4. The peptide of Zhang et al. is alleged to inhibit the interaction of CD4 and MHC, class II, as shown by blockage of antigen induced IL-2 secretion.

3. SUMMARY OF THE INVENTION

The present invention encompasses a method of inhibiting an undesired CD4 T cell immune response in a human subject by administering an effective amount of a compound that blocks the interaction of CD4 and MHC, class II of between 1450 and 400 daltons and preferably between 1400 and 400 daltons. Compounds that inhibit CD4/MHC, class II, interaction can be identified by their ability to block the rosetting of the human B-cells tumor line, Raji, around a cell that expresses CD4, but have no toxic effects, e.g., no effects on the proliferation of transformed cells. The method comprises administering a therapeutically effective amount of a compound that inhibits CD4 oligomer formation, which compound has a molecular weight of between 1450 daltons and 400 daltons, preferably between 1400 daltons and 400 daltons.

The present invention is further directed towards examples of such compounds, such as synthetic peptides that mimic all or a part of: residues 29–35, the C–C' loop of the D1 domain; residues 317–323, the C–C' loop of the D4 domain; and residues 346–353, the CDR3 or FG ridge of the D4 domain of the CD4 molecule and inhibit T cell activation and towards the method of using such peptides to inhibit human CD4dependent immune responses. In a preferred embodiment the peptides of the invention are cyclic peptides. The invention encompasses inhibiting T cell activation by contacting T cells with an effective amount of a peptide that mimics the C–C' loop. Further the invention encompasses methods of treating autoimmune diseases in humans, that are ameliorated by interfering with the function of the CD4 molecule.

4. BRIEF DESCRIPTION OF THE FIGS.

FIG. 1A. Schematic of a general method of synthesis of a macrocyclic peptidomimetic corresponding to a tetrapeptide.

Figure 1B:
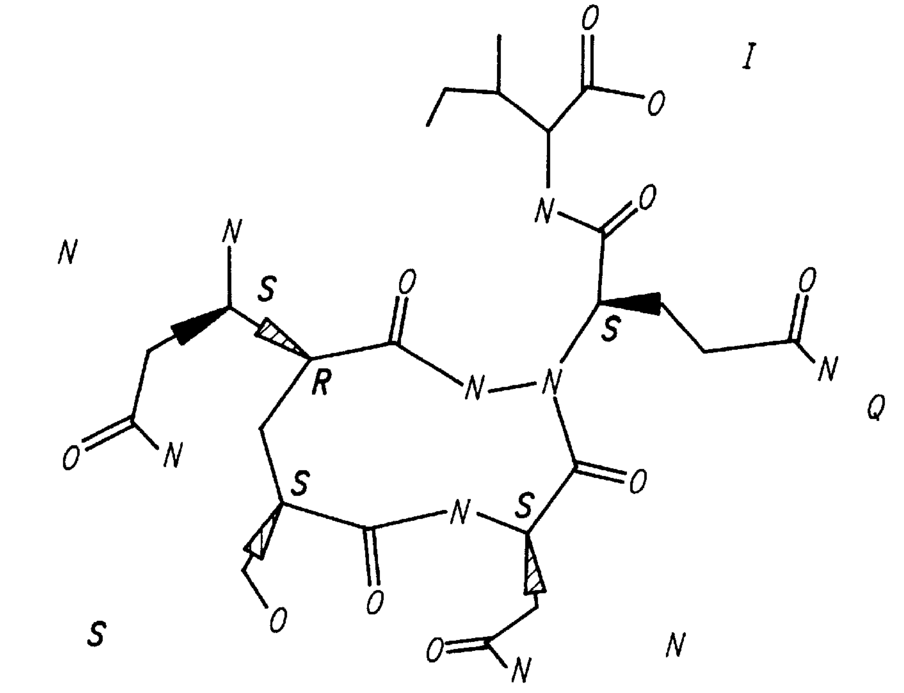

FIG. 1B. Structure of a macrocyclic peptidomimetic corresponding to the pentapepide NSNQI[1]. (SEQ ID NO:1)

[1]The following code is used to designate amino acids: A≈Ala, C≈Cys, D≈Asp, E≈Glu, F≈Phe, G≈Gly, H≈His, I≈Ile, K≈Lys, L≈Leu, M≈Met, N≈Asn, P≈Pro, Q≈Gln, R≈Arg, S≈Ser, T≈Thr, V≈Val, W≈Trp, Y≈Tyr. L-amino acids are represented by UPPER CASE letters and D-amino acids by lower case letters.

Figure 1C:
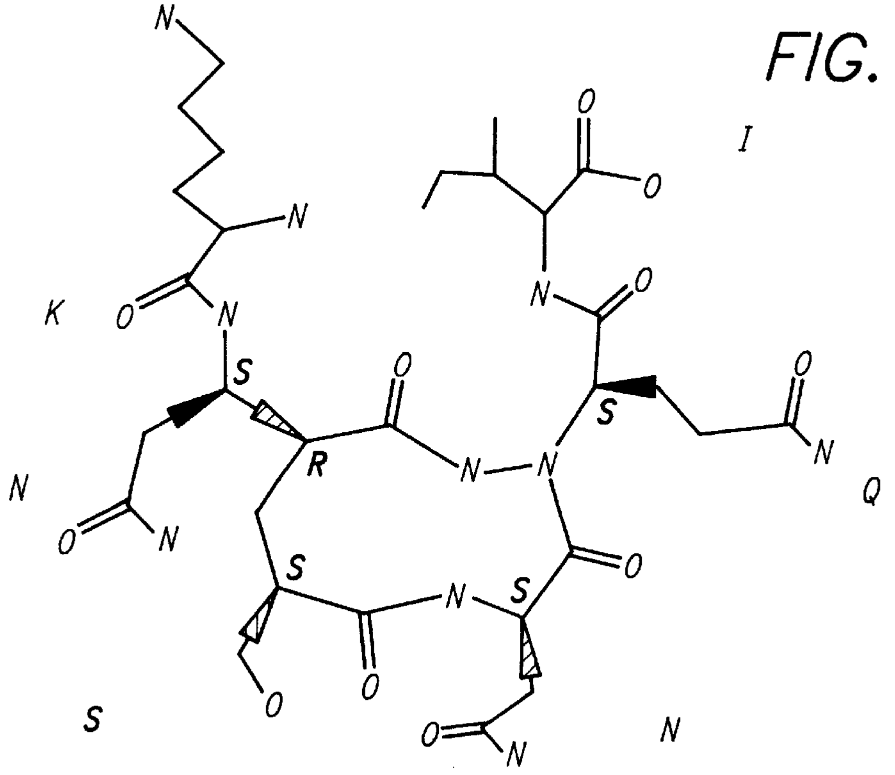

FIG. 1C. Structure of a macrocyclic peptidomimetic corresponding to the hexapeptide KNSNQI. (SEQ ID NO:2)

Figure 2:
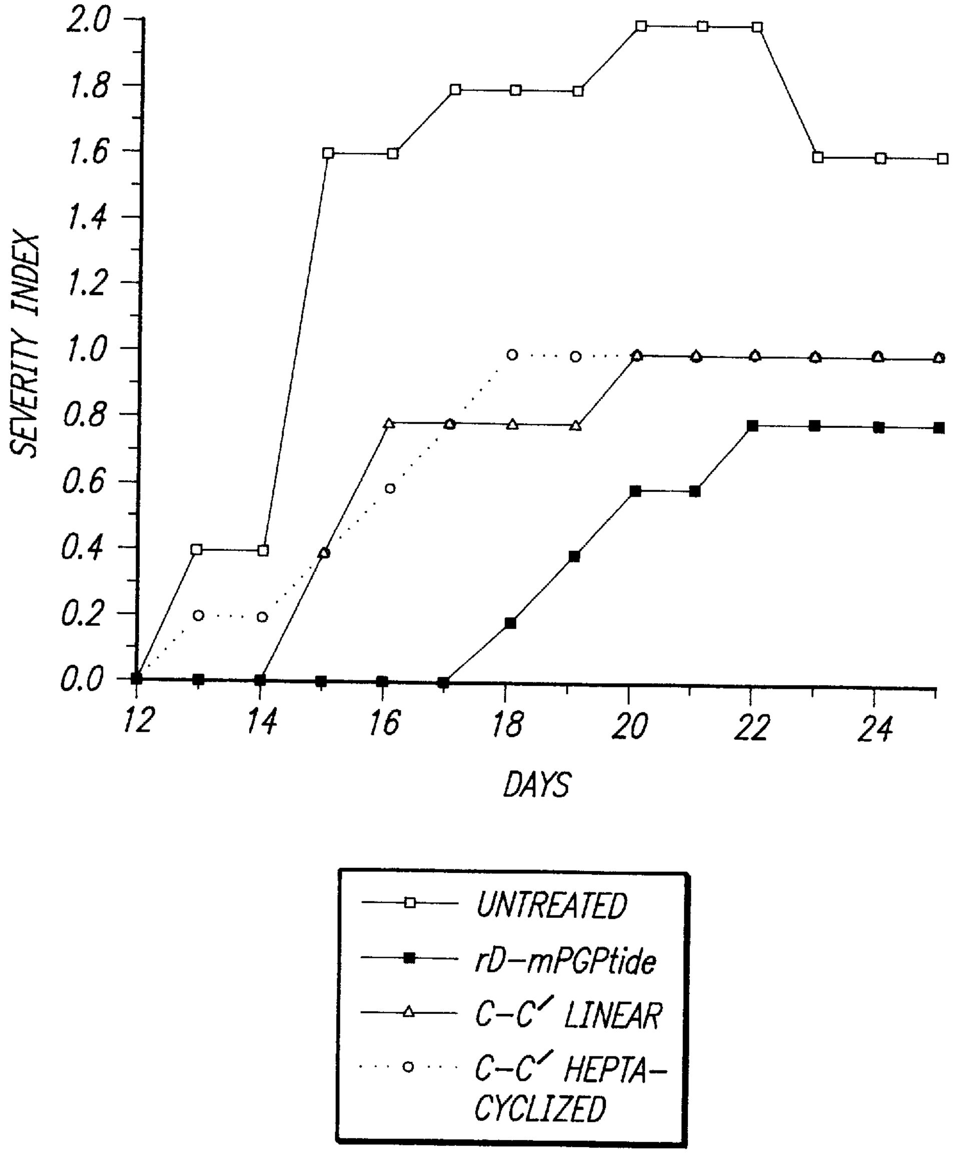

FIG. 2. Comparison among four groups of the severity of clinical signs of a murine EAE model. The groups are: untreated, —□—; treated with rD-mPGPtide positive control, —■—; treated with a linear CNSNQIC (SEQ ID NO:44) peptide, —Δ—; treated with a cyclic CNSNQIC (SEQ ID NO:45) peptide, —○—.

Figure 3:
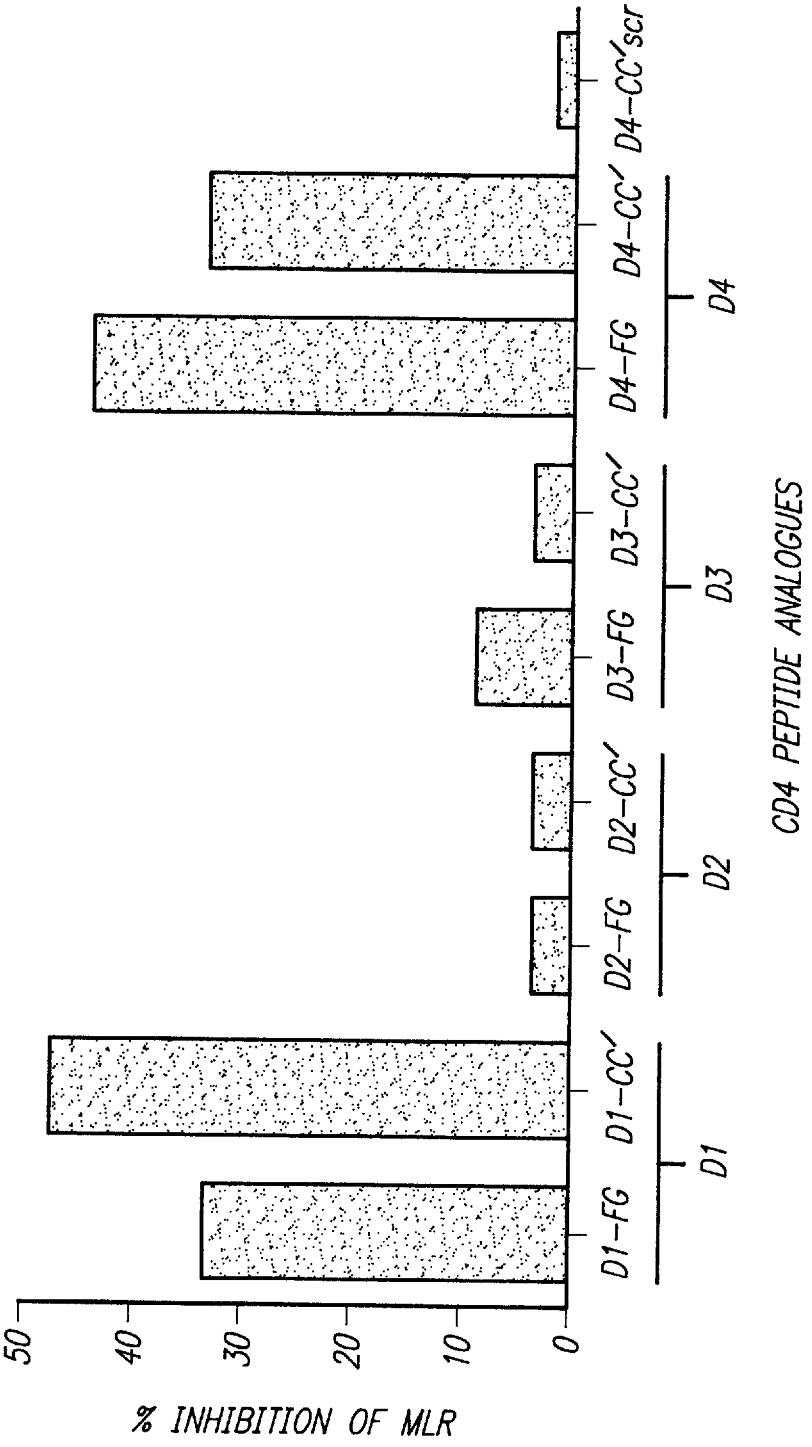

FIG. 3. Inhibition of human allogenic mixed lymphocyte reaction by peptides that mimic portion of CD4.

5. DETAILED DESCRIPTION OF THE INVENTION

The present invention concerns methods of inhibiting human, CD4 T-cell immune responses by administering an effective amount of a compound, the molecular weight of which is between 1450 and 400 daltons, and preferably between 1400 and 400 daltons, that specifically blocks the interaction of CD4 and MHC, class II, gene products. The use of compounds having higher molecular weights is subject to disadvantages in achieving and maintaining a therapeutical effective concentration. In particular embodiments of the invention, the compound is a peptide or peptide mimetic selected to mimic the following sequences of human CD4: KNSNQLIK (SEQ ID NO:3), KNSNQIK (SEQ ID NO:4), NSNQI (SEQ ID NO:1)(Dl–CC' mimics), KLENKEA (SEQ ID NO:5)(D4–CC' mimic) and LSDS-GQVL (SEQ ID NO:6)(D4—FG mimic).

In further embodiments of the invention the compounds are the peptide and peptide mimetics that can be formed by conservative substitutions of the above sequences.

5.1. METHODS OF IDENTIFYING INHIBITORS OF CD4/MHC, CLASS II, INTERACTION

The capacity of a compound to inhibit the interaction of CD4 and MHC, class II, gene products can be determined by a cell rosetting assay. A cell line, such as Cos-7, Cos-1 or the like, can be transiently transfected with a plasmid bearing a human CD4 cDNA operably linked to a promoter. In an alternative embodiment a COS-1 cell line can be stably transformed with a human CD4 expression plasmid. The human CD4 expressing cells and a human MHC, class II, expressing cell are mixed so that cellular rosettes are formed.

Specific blockage by a compound is evidenced by a reduction in the number of rosettes by at least 50% when the compound is present in the rosetting medium at a concentration of at most 200 $\mu$M , and the 50% rosette-inhibitory concentration shows a less than 20% inhibition of the proliferation of transformed cells lines, e.g., EBV-transformed B-lymphoblastoid cell lines or IL-2-dependent T-cell lines, such as HT-2.

In a further embodiment of the invention, the compound that specifically inhibits the interaction of CD4 and MHC, class II, is further characterized by a less than 20% inhibition of LPS-stimulated proliferation or Phytohemagglutinin-stimulated proliferation of peripheral blood lymphocytes at the 50% rosette-inhibiting concentration.

5.2. COMPOUNDS OF THE INVENTION

The present invention provides synthetic peptides that mimic three portions of the human CD4 molecule: residues 29– 35, the C–C' loop of the D1 domain; residues 317–323, the C–C' loop of the D4 domain; and residues 346–353, the FG ridge of the D4 domain of the CD4 molecule. In a preferred embodiment of the invention the synthetic peptide contains a core peptide that mimics the structure of a portion of the CD4 and an N and C terminal residues that allow for the cyclization of the peptide. The cyclic synthetic peptides of the present invention can contain "core" peptide sequences that are common to both the human and murine CD4 molecule or that resemble such sequences.

One aspect of the invention arises out of the discovery that amino acids from the CD4 region 29–35, termed the C–C' loop of the D1 domain (D1–CC') are important in the formation of intermolecular bonds associated with immunological activity. According to the invention, peptides having 3–10 amino acids with amino acid sequences that include sequences correspond to CD4 sequences 29–35 or portions thereof are provided. The sequence of residues 29–35 of CD4 is K-N-S-N-Q-I-K Q-I-K (SEQ ID NO:4). In some embodiments, one or more of CD4 sequences 29–35 may be substituted. In some embodiments, an amino acid residue is inserted between amino acid residues 29–31 or 33–35 in peptides which comprise all or fragments of CD4 sequences 29–35. In peptides which comprise all or fragments of CD4 sequences 29–35 including insertions, amino acid residues may be substituted. Peptides can contain one or more D amino acids. If all D amino acids are used, the sequence is reversed.

One embodiment of the peptides of the invention is a cyclic peptide having a core peptide sequence NSNQI (SEQ ID NO:1), which corresponds to residues 30–34 of the human CD4 protein. Other embodiments are peptides made by substitutions of the prototype core sequence NSNQI (SEQ ID NO:1) according to the formula:

```
N—S—N—Q—I
↑  ↑  ↑  ↑  ↑
Q  T  D  N  L
D  D  E  E  V
   N  Q  M  A
```

For example, according to the formula, the amino-terminal Asn, corresponding to residue 30 of CD4, can be replaced by a Gin or Asp; the Ser, corresponding to residue 31 of CD4, can be replaced by a Thr, Asp or Asn; and so forth. In one embodiment of the invention the core sequence differs from NSNQI (SEQ ID NO:1) prototype core sequence by a single substitution. In further embodiments, the sequence of the core differs from the prototype sequence by two, three, four and five substitutions, respectively.

Yet further embodiments of the peptides of the invention include peptides made by substitutions of a second prototype core sequence KNSNQIK (SEQ ID NO:4) according to the formula:

```
K—N—S—N—Q—I—K
↑  ↑  ↑  ↑  ↑  ↑  ↑
R  Q  T  D  N  L  R
H  D  D  E  E  V  H
      N  Q  M  A
```

According to the formula the amino-terminal Lys, corresponding to residue 29 of CD4, can be replaced by an Arg or His; the Asn, corresponding to residue 30, can be replaced by a Gln or Asp; and so forth. In one embodiment of the invention the core sequence differs from KNSNQIK (SEQ ID NO:4) prototype core sequence by a single substitution. In further embodiments, the sequence of the core differs from the prototype sequence by two, three, four, five, six and seven substitutions, respectively.

In still a further embodiment of the invention, the core sequence corresponding to CD4 amino acid residues 29–35 is modified by the insertion of Leu at the position between amino acid residue 33 and amino acid residue 34 so the core sequence is a third prototype core sequence KNSNQLIK (SEQ ID NO:3). Yet further embodiments of the peptides of the invention include peptides made by substitutions of the prototype core sequence KNSNQLIK (SEQ ID NO:3) according to the formula:

```
K—N—S—N—Q—L—I—K
↑  ↑  ↑  ↑  ↑  ↑  ↑  ↑
R  Q  T  D  N  I  L  R
H  D  D  E  E  V  V  H
      N  Q  M  A  A
```

Preferred embodiments of the invention that relate to peptides that mimic the D1–CC' region include peptides having core sequences as follows:

| | | | |
|---|---|---|---|
| *—N—Q—+ | | *—N—Q—L—+ | |
| *—N—Q—L—I—+ | SEQ ID NO: 7 | *—N—Q—L—I—K—+ | SEQ ID NO: 9 |
| *—N—Q—I—+ | | *—N—Q—I—K—+ | SEQ ID NO: 9 |
| *—S—N—+ | | *—S—N—Q—L—+ | SEQ ID NO: 10 |
| *—S—N—Q—L—I—+ | SEQ ID NO: 11 | | |
| *—S—N—Q—L—I—K—+ | SEQ ID NO: 12 | | |
| *—S—N—Q—I—+ | SEQ ID NO: 13 | *—S—N—Q—I—K—+ | SEQ ID NO: 14 |
| *—N—S—N—+ | | *—N—S—N—Q—+ | SEQ ID NO: 15 |
| *—N—S—N—Q—L—+ | SEQ ID NO: 16 | | |
| *—N—S—N—Q—L—I—+ | SEQ ID NO: 17 | | |
| *—N—S—N—Q—L—I—K—+ | SEQ ID NO: 18 | | |
| *—N—S—N—Q—I—K—+ | SEQ ID NO: 19 | | |
| *—K—N—S—N—+ | SEQ ID NO: 20 | *—K—N—S—N—Q—+ | SEQ ID NO: 21 |
| *—K—N—S—N—Q—L—+ | SEQ ID NO: 22 | | |
| *—K—N—S—N—Q—L—I—+ | SEQ ID NO: 23 | | |
| *—K—N—S—N—Q—L—I—K—+ | SEQ ID NO: 4 | | |
| *—K—N—S—N—Q—I—+ | SEQ ID NO: 2 | | |
| *—K—N—S—N—Q—I—K—+ | SEQ ID NO: 4 | | |

wherein each amino acid is an L-amino acid and the symbols * and + designate the N-terminal and C-terminal, respectively.

Preferred peptides are those having the following core sequences:

| | | | |
|---|---|---|---|
| *—E—N—K—+ | | *—E—N—K—E—+ | SEQ ID NO: 24 |
| *—E—N—K—E—A—+ | SEQ ID NO: 25 | *—L—E—N—K—+ | SEQ ID NO: 26 |
| *—L—E—N—K—E—+ | SEQ ID NO: 27 | *—L—E—N—K—E—A—+ | SEQ ID NO: 28 |
| *—K—L—E—N—K—+ | SEQ ID NO: 29 | *—K—L—E—N—K—E—+ | SEQ ID NO: 30 |
| *—K—L—E—N—K—E—A—+ | SEQ ID NO: 5 | | |

wherein * and + are as above.

A further aspect of the invention arises out of the discovery that amino acids from the CD4 region 317–323 are important in the formation of intermolecular bonds associated with immunological activity. This region is termed the CC' loop of the D4 domain of CD4 (D4–CC') and its sequence is K-L-E-N-K-A (SEQ ID NO:5). According to the invention, peptides having 3–9 amino acids with amino acid sequences that include sequences correspond to CD4 sequences 317–323 or portions thereof are provided. According to the invention, peptides having 3–9 amino acids with amino acid sequences that include sequences correspond to CD4 sequences 317–323 or portions thereof are provided. In some embodiments, one or more of CD4 sequences 317–323 may be substituted.

In the peptides of the invention, the amino acids corresponding to CD4 amino acid residues 317–323 may be substituted as follows:

| K | L | E | N | K | E | A |
|---|---|---|---|---|---|---|
| ↑ | ↑ | ↑ | ↑ | ↑ | ↑ | ↑ |
| R | I | D | Q | R | D | V |
| H | V | N | D | H | N | G |
| | Q | | | Q | | |

Peptides can contain D amino acids. If all D amino acids are used, the sequence is reversed. Peptides of the invention comprise a 3 or more amino acid fragment preferably comprise amino acid sequences corresponding to CD4 sequence 319–321 E-N-K. The peptides may comprise CD4 sequence 319–321 E-N-K or they may have one or more substitutions as defined above. Peptides can include peptides with amino acid sequence corresponding to CD4 amino acid sequences 319–321, 319–322, 319–323, 318–321, 318–322, 318–323, 317–321, 317–322, 317–323. The peptides may comprise one or more D amino acid residues. If the peptide comprises all D amino acid residues, it has a reverse sequence.

A further aspect of the invention arises out of the discovery that amino acids from the CD4 region 346–353 are important in the formation of intermolecular bonds associated with immunological activity. This region is termed the FG ridge of the D4 domain (D4-FG) and its sequence is L-S-D-S-G-Q-V-L (SEQ ID NO:6). According to the invention, peptides having 3–9 amino acids with amino acid sequences that include sequences correspond to CD4 sequences 346–353 or portions thereof are provided. In some embodiments, one or more of CD4 sequences 346–353 may be substituted. Peptides can contain one or more D amino acids. If all D amino acids are used, the sequence is reversed.

In the peptides of the invention, the amino acids corresponding to CD4 amino acid residues 346–353 may be substituted as follows.

| L | S | D | S | G | Q | V | L |
|---|---|---|---|---|---|---|---|
| ↑ | ↑ | ↑ | ↑ | ↑ | ↑ | ↑ | ↑ |
| I | T | E | T | D | N | L | I |
| V | D | Q | D | | E | I | V |
| | | | G | | K | | K |

Peptides can include peptides with amino acid sequence corresponding to CD4 amino acid sequences 349–351, 349–352, 349–353, 348–351, 348–352, 348–353, 347–351, 347–352, 347–353, 346–351, 346–352, 346–353 including all CD4 sequence residues or one or more substitutions as defined above and with or without N and C termini cyclizing residues or moieties. Preferred peptides are those having the following core sequences:

| | | | |
|---|---|---|---|
| *—S—G—Q—+ | | *—S—G—Q—V—+ | SEQ ID NO: 31 |
| *—S—G—Q—V—L—+ | SEQ ID NO: 32 | *—D—S—G—Q—+ | SEQ ID NO: 33 |
| *—D—S—G—Q—V—+ | SEQ ID NO: 34 | *—D—S—G—Q—V—L—+ | SEQ ID NO: 35 |
| *—S—D—S—G—Q—+ | SEQ ID NO: 36 | *—S—D—S—G—Q—V—+ | SEQ ID NO: 37 |
| *—S—D—S—G—Q—V—L—+ | SEQ ID NO: 38 | | |
| *—L—S—D—S—G—Q—+ | SEQ ID NO: 39 | | |
| *—L—S—D—S—G—Q—V—+ | SEQ ID NO: 40 | | |
| *—L—S—D—S—G—Q—V—L—+ | SEQ ID NO: 6 | | |

wherein * and + are as above.

In these peptides, any one or more of the amino acids, including N and/or C terminal residues, may be a D amino acid. If all of the amino acids are D amino acids, the order from N to C termini is reversed.

In one embodiment of the invention the core sequence differs from the prototype core sequence by a single substitution. In further embodiments, the sequence of the core differs from the prototype sequence by two, three, four, five, six, seven and eight substitutions, respectively.

Further embodiments of the invention include the homologs of the first, second and third prototype core sequences consisting of d-amino acids linked in the reverse order, i.e., the sequences, from N→C, of: iqnsn, kiqnsnk and kilqnsnk. The residues of the d-amino acid containing core sequences correspond to residues of the CD4, but in the reverse order, e.g., in the sequence kiqnsnk, the Lys adjacent to Ile corresponds to CD4 residue 35 and the Lys adjacent to Asn corresponds to CD4 residue 29. Also included within the peptides of the invention are embodiments having one, two, three etc. up to eight substitutions exactly according to the formulas given above except for the use of d-amino acids as replacement amino acids. Thus, for example, the dAsn, corresponding to residue 30, can be replaced by dGln or dasp; the dser, corresponding to residue 31 by dThr, dAsp or dasn; and so forth.

A further embodiment of the invention consists of the uncyclized core peptides alone, and their use to suppress a human CD4 T-cell immune response.

Thus, as set forth above, in one embodiment, the core sequence from N-terminal to C-terminal is Asn-Ser-Asn-Gln-Ile (NSNQI) (SEQ ID NO:1) and in a second embodiment the core sequence is Ser-Asn-Gln (SNQ). Each amino acid in the core sequences is an L-amino acid. Alternatively, a cyclic synthetic peptide of the present invention can have a "core" sequence which is the reverse of one of the above-noted core sequences, i.e., from N-terminal to C-terminal, IQNSN and QNS. When the core sequence is reversed, each amino acid of the core sequence is a D-amino acid.

It was found that the synthetic peptide CNSNQIC (SEQ ID NO:44), which was cyclized by intramolecular oxidation of the cysteines to a cystine, was a highly potent inhibitor of human T cell proliferation, in vitro, as well as an inhibitor of EAE in mice.

The cyclic structures of the peptides of the invention enhance their structural stability, so that the peptides more closely mimic the conformation of the C–C' loop of the native CD4 molecule. To cyclize the peptide, the peptide is provided with a first amino acid adjacent to the N-terminal and a second amino acid C-terminal of the "core" sequence. Accordingly, the amino acids adjacent to the N-terminal and C-terminal can be any amino acids that form a bond with each other. The amino acids can each be either cysteine or penicillamine, and the molecule is cyclized by the formation of a disulfide bond.

According to the invention, there can be optionally present an additional 1 to 3 amino acids at either the N-terminal or the C-terminal of the core sequence or both. These amino acids can be selected from the group consisting of Y, W, F, I and L, and preferably the selection is without replacement, i.e., the terminal peptides do not contain repeated amino acids.

Without limitation as to theory, the compounds of the invention are believed to mimic a portion of the surface of CD4. The compounds of the invention inhibit antigen dependent T cell activation and thereby can be used in the treatment and prevention of disorders and conditions characterized by undesirable T cell activation.

In one embodiment, the peptides of the invention, which contain the above-noted core sequence NSNQI (SEQ ID NO:1), can be represented by the following general formula:

N(H)(R')—X' Z' N S N Q I Z" X"—CO—R"

in which:

(a) N(H)(R') is the amino terminal, wherein R' is either acetyl or hydrogen, and CO—R" is the carboxyl terminal, wherein R" is either $NH_2$ or OH;

(b) each of N, S, Q and I is an L-amino acid;

(c) X' is present or absent, and, if present, is an L-amino acid or a di- or tripeptide of L-amino acids selected from the group consisting of Y, W, and F, provided that no amino acid is selected more than once;

(d) X" is present or absent, and if present, is an L-amino acid selected from the group of consisting of Y, W, F, I, L or a dipeptide of L-amino acids selected from the group consisting of L and I;

(e) Z' and Z" are amino acids that are linked to each other so that the peptide is a cyclic peptide. Preferred examples of this embodiment are follows:

| | R' | R" | X' | X" | Z'/Z" |
|---|---|---|---|---|---|
| 1. | H | OH | Y | Absent | Cys |
| 2. | H | OH | WHF | Absent | Cys |

Further embodiments, the peptides of the invention, which contain the core sequence SNQ, can be represented by the following general formula:

N(H)(R')—X'Z'S N Q Z"X"—CO—R"

in which:

a) N(H)(R') is the amino terminal, wherein R' is acetyl or hydrogen; and CO—R" is the carboxyl terminal, wherein R" is $NH_2$ or OH;

b) each of N, S and Q is an L-amino acid;

c) X' is present or absent, and, if present, is an L-amino acid or a di- or tripeptide of L-amino acids selected from the group consisting of Y, W, and F, provided that no amino acid is selected more than once;

d) X" is present or absent, and if present is an L-amino acid selected from the group of consisting of Y, W, F, I, L or a dipeptide of L-amino acids selected from the group consisting of L and I;

e) Z' and Z" are amino acids that are linked to each other so that the peptide is a cyclic peptide. Preferred examples of this embodiment are follows:

| | R' | R" | X' | X" | Z'/Z" |
|---|---|---|---|---|---|
| 1. | Acetyl | OH | Y | Absent | Cys |
| 2. | Acetyl | OH | WHF | Absent | Cys |

In an alternative embodiment, the peptides of the invention can be comprised of D-amino acids. The use of D-amino acids has the advantage of increased resistance to degradation in the host. In one embodiment the peptides of the invention, which contain the core sequence iqnsn, can be represented by the following general formula:

N(H)(R')—X"Z"i q n s n Z'X'—CO—R"

in which:

(a) N(H)(R') is the amino terminal, wherein R' is either acetyl or hydrogen, and CO–R" is the carboxyl terminal, wherein R" is $NH_2$ or OH;;

(b) each of n, s, q and i is an D-amino acid;

(c) X' is present or absent, and, if present, is a D-amino acid or a di- or tripeptide of D-amino acids selected from the group consisting of y, w, and f, provided that no amino acid is selected more than once;

(d) X" is present or absent, and if present is a D-amino acid selected from the group of consisting of y, w, f, i, l or a dipeptide of D-amino acids selected from the group consisting of L and I;

(e) Z' and Z" are amino acids that are linked to each other so that the polypeptide is a cyclic polypeptide. Preferred examples of this embodiment are follows:

| | R' | R" | X' | X" | Z'/Z" |
|---|---|---|---|---|---|
| 1. | H | OH | y | Absent | cys |
| 2. | H | OH | whf | Absent | cys |

Further embodiments of the invention, which contain the core sequence qns, can be represented by the following general formula:

N(H)(R')—X"Z"q n s Z'X'—CO—R"

in which:

a) N(H)(R') is the amino terminal, wherein R' is acetyl or hydrogen, and CO—R" is the carboxyl terminal, wherein R" is $NH_2$ or OH;

b) each of n, s and q is a D-amino acid;

c) X' is present or absent, and, if present, is a D-amino acid or a di- or tripeptide of D-amino acids selected from the group consisting of y, w, and f, provided that no amino acid is selected more than once;

d) X" is present or absent, and if present is a D-amino acid selected from the group of consisting of y, w, f, i, l or a dipeptide of D-amino acids selected from the group consisting of L and I;

e) Z' and Z" are an amino acids that are linked to each other so that the peptide is a cyclic peptide. Preferred examples of this embodiment are follows:

| | R' | R" | X' | X" | Z'/Z" |
|---|---|---|---|---|---|
| 1. | Acetyl | OH | y | Absent | cys |
| 2. | Acetyl | OH | fhw | Absent | cys |

Additional embodiments of the invention can be determined by placing each of the above recited preferred sequences into the foregoing formula.

Thus, embodiments of the invention are peptides according to the above formula wherein the core peptide is selected from the group of peptides:

| | | | |
|---|---|---|---|
| *—N—Q—+ | | *—N—Q—L—+ | |
| *—N—Q—L—I—+ | SEQ ID NO: 7 | *—N—Q—L—I—K—+ | SEQ ID NO: 8 |
| *—N—Q—I—+ | | *—N—Q—I—K—+ | SEQ ID NO: 9 |
| *—S—N—+ | | *—S—N—Q—L—+ | SEQ ID NO: 10 |
| *—S—N—Q—L—I—+ | SEQ ID NO: 11 | | |
| *—S—N—Q—L—I—K—+ | SEQ ID NO: 12 | | |
| *—S—N—Q—I—+ | SEQ ID NO: 13 | *—S—N—Q—I—K—+ | SEQ ID NO: 14 |
| *—N—S—N—+ | | *—N—S—N—Q—+ | SEQ ID NO: 15 |
| *—N—S—N—Q—L—+ | SEQ ID NO: 16 | | |
| *—N—S—N—Q—L—I—+ | SEQ ID NO: 17 | | |
| *—N—S—N—Q—L—I—K—+ | SEQ ID NO: 18 | | |
| *—N—S—N—Q—I—K—+ | SEQ ID NO: 19 | | |
| *—K—N—S—N—+ | SEQ ID NO: 20 | | |
| *—K—N—S—N—Q—+ | SEQ ID NO: 21 | | |
| *—K—N—S—N—Q—L—+ | SEQ ID NO: 22 | | |
| *—K—N—S—N—Q—L—I—+ | SEQ ID NO: 23 | | |
| *—K—N—S—N—Q—L—I—K—+ | SEQ ID NO: 3 | | |
| *—K—N—S—N—Q—I—+ | SEQ ID NO: 2 | | |
| *—K—N—S—N—Q—I—K—+ | SEQ ID NO: 4 | | |
| *—E—N—K—+ | | *—E—N—K—E—+ | SEQ ID NO: 24 |
| *—E—N—K—E—A—+ | SEQ ID NO: 25 | *—L—E—N—K—+ | SEQ ID NO: 26 |
| *—L—E—N—K—E—+ | SEQ ID NO: 27 | | |
| *—L—E—N—K—E—A—+ | SEQ ID NO: 28 | *—K—L—E—N—K—+ | SEQ ID NO: 29 |
| *—K—L—E—N—K—E—+ | SEQ ID NO: 30 | | |
| *—K—L—E—N—K—E—A—+ | SEQ ID NO: 5 | | |
| *—S—G—Q—+ | | *—S—G—Q—V—+ | SEQ ID NO: 31 |

-continued

| | |
|---|---|
| *—S—G—Q—V—L—+ | SEQ ID NO: 32 |
| *—D—S—G—Q—+ | SEQ ID NO: 33 |
| *—D—S—G—Q—V—+ | SEQ ID NO: 34 |
| *—D—S—G—Q—V—L—+ | SEQ ID NO: 35 |
| *—S—D—S—G—Q—+ | SEQ ID NO: 36 |
| *—S—D—S—G—Q—V—+ | SEQ ID NO: 37 |
| *—S—D—S—G—Q—V—L—+ | SEQ ID NO: 38 |
| *—L—S—D—S—G—Q—+ | SEQ ID NO: 39 |
| *—L—S—D—S—G—Q—V—+ | SEQ ID NO: 40 |
| *—L—S—D—S—G—Q—V—L—+ | SEQ ID NO: 6 |

wherein, * and + designate the amino and carboxyl termini of the core peptide, respectively.

Further embodiments of the invention include peptides having core peptides containing D-amino acids according to the following formulae:

| | |
|---|---|
| *—n—q—+ | *—n—q—l—+ |
| *—n—q—l—i—+ | *—n—q—l—i—k—+ |
| *—n—q—i—+ | *—n—q—i—k—+ |
| *—s—n—+ | *—s—n—q—l—+ |
| *—s—n—q—l—i—+ | *—s—n—q—l—i—k—+ |
| *—s—n—q—i—+ | *—s—n—q—i—k—+ |
| *—n—s—n—+ | *—n—s—n—q—+ |
| *—n—s—n—q—l—+ | *—n—s—n—q—l—i—+ |
| *—n—s—n—q—l—i—k—+ | *—n—s—n—q—i—k—+ |
| *—k—n—s—n—+ | *—k—n—s—n—q—+ |
| *—k—n—s—n—q—l—+ | *—k—n—s—n—q—l—i—+ |
| *—k—n—s—n—q—l—i—k—+ | *—k—n—s—n—q—i—+ |
| *—k—n—s—n—q—i—k—+ | |
| *—e—n—k—+ | *—e—n—k—e—+ |
| *—e—n—k—e—a—+ | *—l—e—n—k—+ |
| *—l—e—n—k—e—+ | *—l—e—n—k—e—a—+ |
| *—k—l—e—n—k—+ | *—k—l—e—n—k—e—+ |
| *—k—l—e—n—k—e—a—+, | |
| *—s—g—q—+ | *—s—g—q—v—+ |
| *—s—g—q—v—l—+ | *—d—s—g—q—+ |
| *—d—s—g—q—v—+ | *—d—s—g—q—v—l—+ |
| *—s—d—s—g—q—+ | *—s—d—s—g—q—v—+ |
| *—s—d—s—g—q—v—l—+ | *—l—s—d—s—g—q—+ |
| *—l—s—d—s—g—g—v—+ | *—l—s—d—s—g—q—v—l—+, |

wherein, * and + designate the carboxyl and amino termini of the core peptide, respectively. In yet a further embodiment of the invention the peptides of the invention can be replaced by corresponding peptidomimetics that contain a 10 member heterocyclic ring.

Peptidomimetics can be synthesized as described in Nakanishi et al., 1993, Gene 137:51–56, which is incorporated herein by reference. The preparation of the peptidomimetics can be achieved by either the solid-phase peptide synthesis or the solution phase synthesis. The heterocyclic ring is formed by the reaction of an activated, 4-member azetidinone ring and a hydrazino moiety to effect the macrocyclization reaction. In the solid-phase synthesis, an alloc group can be used to protect the hydrazino group which can be removed by the Pd catalyst. The alloc group is orthogonal to Fmoc protecting groups and, hence is compatible with the solid-phase peptide synthesis scheme described above.

FIG. 1A shows a general scheme for the solid-phase synthesis of a macrocyclic peptidomimetic having four side-chains. FIG. 1B shows an example of a peptidomimetic of the invention; the side chains of the peptidomimetic correspond to Asn, Ser, Asn, Gln with a C-terminal Ile. The peptidomimetic shown in FIG. 1B corresponds to the peptide NSNQI (SEQ ID NO:1) which is CD4 residues 30–34. FIG. 1C shows a further example of a peptidomimetic of the invention. The peptidomimetic shown corresponds to the peptide KNSNQI (SEQ ID NO:3) which is CD4 residues 29–34. Peptidomimetics corresponding to any of the other 4, 5 and 6 amino acid peptides described herein may be synthesized by the same technique.

The resulting macrocyclic peptidomimetics of a tetrameric, pentameric or hexameric peptides, following the formula:

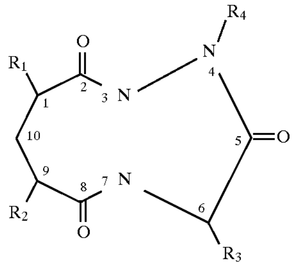

When the peptidomimetic corresponds to a tetrapeptide then $R_1$ corrsponds to the α-carbon, amine and side chain of the amino terminal amino acid, $R_2$ corresponds to the side-chain of the second amino acid, $R_3$ corresponds to the side chain of the third amino acid, 4-N coresponds to the amino nitrogen of the 4th amino terminal amino acid and $R_4$ corresponds to the α-carobon, side chain and caroxyl moiety of the carboxyl terminal amino acid. A pentameric peptidomimetic can be constructed by incorporating the carboxyl terminal amino acid into the $R_4$ substituent by a peptide bond at the carboxyl moiety, or by incorporating the amino terminal amino acid into the $R_1$ substituent by a peptide bond to the amino group. A hexameric peptidomimetic can be constructed by extending $R_1$ and $R_4$ to include the amino terminal and carboxyl terminal amino acids, respectively.

The peptidomimetics of the invention can be formulated, administered and used as described herein in place of peptides.

Each of the peptides of the invention can be used to suppress undesired immune responses in mice and humans. For example, autoimmune diseases such as rheumatoid arthritis, multiple sclerosis, and SLE can be treated by administration of compounds of the present invention to a subject having one such. The dose of peptide needed to treat a subject can be determined by methods well known to those skilled in the art from the observations that the cyclic peptide CNSNQIC (SEQ ID NO:45) inhibited a murine and human mixed lymphocyte reaction at between about 50 μM and 200 μM and that a 0.5 mg dose the CNSNQIC (SEQ ID NO:45) peptide, when given i.v. 12 days after immunization, is effective to ameliorate EAE in a mouse.

The compounds of the invention can be administered to a subject who has received an allogeneic graft, e.g., bone marrow, kidney or pancreas. The rejection of the graft can thereby be avoided. The peptides of the invention can be used in conjunction with immunosuppressive agents, well known to those skilled in the art. Peptides of the invention can be advantageously administered to a patient either prior to transplantation or later. Peptides of the present invention can be administered to patients suffering from graft versus host disease to inhibit the disease.

The peptides of the present invention can be prepared by any technique known or to be developed later. The peptides can be prepared using the solid-phase synthetic technique described by Merrifield, in *J. Am. Chem. Soc.,* 15:2149–2154 (1963); in M. Bodanszky et al., (1976). *Peptide Synthesis*, John Wiley & Sons, 2d Ed.; Kent and Clark-Lewis in *Synthetic Peptides in Biology and Medicine,* p. 295–358, eds. Alitalo, K., et al. Science Publishers, (Amsterdam, 1985); as well as other reference works known to those skilled in the art. A summary of peptide synthesis techniques may be found in J. Stuart and J.D. Young, *Solid Phase Peptide Synthesis* , Pierce Chemical Company, Rockford, IL (1984). The synthesis of peptides by solution methods may also be used, as described in The Proteins, Vol. II, 3d Ed., p. 105–237, Neurath, H., et al., Eds., Academic Press, New York, N.Y. (1976). Appropriate protective groups for use in such syntheses will be found in the above texts, as well as in J. F. W. McOmie, *Protective Groups in Organic Chemistry,* Plenum Press, New York, N.Y. (1973).

In general, the synthesis of the peptides involves the sequential addition of one or more amino acid residues or suitable protected amino acid residues to a growing peptide chain. Typically, the carboxyl group of the first amino acid residue is pre-attached to a solid support, the amino group being protected by a first, selectively-removable protecting group. A second, different, selectively removable protecting group is utilized with amino acids containing a reactive side group, such as lysine. After the removal of the first protecting group, the carboxyl group of the second amino acid is coupled to the amino group of the first amino acid. The process is then repeated until the peptide is complete, at which time the peptide is removed from the solid support.

Cyclization can be by means of disulfide bridges between cysteine residues, penicillamine residues or cysteine and penicillamine residues. Cysteine residues, penicillamine residues or cysteine and penicillamine residues can be included in positions on the peptide that flank the portions of the core sequences. Intramolecular disulfides form spontaneously by dissolving the peptides, having two sulfhydrals moieties, at about 100 $\mu$g/ml in 0.1M $NH_4HCO_3$ and stirring overnight with exposure to room air at 22° C. Alternatively, the peptides can be cyclized by forming an amide bond between an amino acid at or near the amino and an amino acid at or near the carboxyl termini, or by addition of a glycine linker between such amino acids. Cyclization can also be accomplished as taught in Huang, Z., et al., 1992, *J. Am. Chem. Soc.* 114:9390–9401, which is incorporated herein by reference.

The peptides of the invention are shown to be effective to treat autoimmune disease by the results of two assays: the peptides inhibit T cell proliferation in an MLR of human or murine T cells; and the peptides ameliorate EAE in mice.

The present invention provides pharmaceutical compositions that comprise the compounds of the invention and pharmaceutically acceptable carriers or diluents.

For parenteral administration, the peptides of the invention can be, for example, formulated as a solution, suspension, or lyophilized powder in association with a pharmaceutically acceptable parenteral vehicle. Examples of such vehicles are water, saline, Ringer's solution, dextrose solution, and 5% human serum albumin. The vehicle or lyophilized powder may contain additives that maintain isotonicity (e.g., sodium chloride, mannitol) and chemical stability (e.g., buffers and preservatives). For example, a parenteral composition suitable for administration by injection is prepared by dissolving 1.5% by weight of active ingredient in 0.9% sodium chloride solution. The formulation can be sterilized by any commonly used technique.

The pharmaceutical compositions according to the invention may be administered as a single dose or in multiple doses. The pharmaceutical compositions of the present invention may be administered either as individual therapeutic agents or in combination with other therapeutic agents. The treatments of the present invention may be combined with conventional therapies, which may be administered sequentially or simultaneously.

The pharmaceutical compositions of the present invention may be administered by any means that enables the active agent to reach the targeted cells. Because peptides are subject to being digested when administered orally, parenteral administration, i.e., intravenous, subcutaneous or intramuscular, would ordinarily be used to optimize absorption. Intravenous administration may be accomplished with the aid of an infusion pump. Alternatively, the peptides can be formulated as aerosol medicaments for intranasal inhalation or topical administration.

The dosage administered varies depending upon factors such as: pharmacodynamic characteristics; its mode and route of administration; age, health, and weight of the recipient; nature and extent of symptoms; kind of concurrent treatment; and frequency of treatment. Usually, the dosage of peptide can be about 1 to 3000 milligrams per 50 kilograms of body weight; preferably 10 to 1000 milligrams per 50 kilograms of body weight; more preferably 25 to 800 milligrams per 50 kilograms of body weight. Ordinarily 8 to 800 milligrams are administered to an individual per day in divided doses 1 to 6 times a day or in sustained release form is effective to obtain desired results.

EXAMPLES

Example 1

Synthesis and Characterization of a C–C' loop Cyclic Heptapeptide: CNSNQIC

The peptide CNSNQIC (SEQ ID NO:45) was synthesized using conventional methods of peptide synthesis. Peptides were synthesized on an Applied Biosystem (Foster City, Calif.) 430A fully automated peptide synthesizer according to methods of Jameson et al., 1988, Science 240:1335. The peptides containing internal cysteine residues were refolded and oxidized by dissolving them at 100 $\mu$g/ml in 0.1 M $NH_4HCO_3$ and stirring overnight exposed to air at 23° C. The peptides show greater than 95% intramolecular disulfide bonding at the end of this procedure as monitored by Ellmans reagents, HPLC analysis and gel filtration. Peptides were lyophilized, resuspended in complete medium and filtered through a 0.22 $\mu$ filter prior to use in biological assays.

The peptide was characterized by analytical HPLC analysis, mass spectrometry analysis, and high resolution 600 MHz NMR spectroscopy. The analysis of this synthetic peptide showed that its purity was >99%. HPLC was carried out an analytical HPLC Vydac C18 column (25×4.6 mmI.D., 5 $\mu$m spherical packing at flow rate of 1 ml/min.), which UV detection at 206 nm. Two solvents: solvent A (deionized water/0.1% TFA) and solvent B (Acetonitrile/0.1% TFA) were used.

Mass spectrometry was carried out for CNSNQIC (SEQ ID NO:45) using matrix-assisted laser-desorption mass spectrometry (MALD-MS, LDI-1700, Biomolecular Separations, Ltd., Nevada) with sinapinic acid solution as a matrix. Three major peaks were visible. The peak at 772.8 corresponded to the molecular ion and the other two peaks, 796.0 and 812.8, corresponded to its sodium and potassium salts, respectively.

Example 2

Synthesis of the peptide: YCNSNQIC

The peptide YCNSNQIC (SEQ ID NO:53) was synthesized and tested in vitro in human and murine MLR assay and, in vivo, in an EAE protocol. The peptide was found to have inhibitory activity comparable to the cyclic peptide CNSNQIC (SEQ ID NO:45).

Example 3.

Human mixed lymphocyte reaction (MLR) assay

For this assay, fresh peripheral blood lymphocytes from two different donors are co-cultured; the cells of one donor were irradiated and served as stimulators. Proliferation of these activated T cells was measured by measuring the incorporation of $^3$H-thymidine at various timepoints.

For human MLR, 50 ml of whole blood was collected into anti-coagulant (ACD, acid citrate dextrose) containing tubes. In 50 ml conical tubes, 20 ml of blood was layered over 20 ml Ficoll 1077 (Sigma Chemical Co., St. Louis, Mo.) and centrifuged at 2000 rpm for 35–40 min at 15°–20° C. Buffy coats and serum were collected in 3×volume of PBS centrifuged at 1500 rpm for 15 min at 15°–20° C. Supernatants were discarded, cells were washed 2× in 50 ml PBS and resuspended in RPMI supplemented with 10% heat-inactivated (56°, 30 min) human serum (cat#H4522, Sigma), 50 IU/ml pen/strep and 2mM (1% of 200 mM stock) L-glutamine (both from BioWhitaker). Lymphocyte yield varied between 5–8x$10^7$.

In a 96-well flat bottom plate 1x$10_5$ responders were plated with 2x$10^5$ irradiated (3000 rad) simulators/well (added in 100 μl each), and incubated for 6, 7 or 8 days at 37° C., 7% $CO_2$. Peptide analogues were added to quadruplicate wells, at a concentration of 100 μM (5 mg/ml stock) or titrations thereof, immediately after cells were plated. For radiolabelling, the cells were incubated with 1 μCi [$^3$H]TdR/well (25 μl) (diluted from 1mCi/ml stock, Amersham) for the final 6 hours of incubation. Cells were harvested using a fiberfilter cell harvester (e.g., Harvester 96, Tomtec) and counted in a Beta Counter of Beta plate reader (1205 BS Betaplate Liquid Scintillation Counter, Wallac) with scintillation fluid.

The C–C' loop cyclic heptapeptide CNSNQIC (SEQ ID NO:45) exhibited at least 50% inhibition of responder cell alloreactive proliferation at 100 μM. This cyclic peptide showed significantly higher activity than the linear peptides, KNSNQI (SEQ ID NO:3), KNSNQ (SEQ ID NO:21) and NSNQI (SEQ ID NO:1) which were derived from the same C–C' region.

In order to characterize the specificity and conformational dependence of the observed immunosuppressive effects of the cyclic peptide CNSNQIC (SEQ ID NO:45), two different, related peptides were used as controls. The first control peptide retained the same amino acid composition as the C–C' cyclic heptapeptide, but had its sequence order randomized. The second control peptide was identical in amino acid sequence to the C–C' cyclic heptapeptide but lacked the conformationally restraining Cys-Cys disulfide bridge. These control peptides were tested for their suppressive effect on human T cell activation. The linear peptide showed much lower activity (32.2% inhibition) than the cyclic peptide (54.4% inhibition) while the randomized peptide was completely inactive. These studies demonstrated that a proper amino acid sequence in the context of a three-dimensional conformation is necessary for biological activity of the C–C' cyclic heptapeptide.

Example 4

Murine Mixed Lymphocyte Reaction

Mice were sacrificed and spleens aseptically removed. Cell suspensions were made by gently pressing spleens through nylon mesh, washing cells with RPMI 1640 and hypotonic lysis of red blood cells. After 3 washes in RPMI 1640, cells were resuspended in complete medium (RPMI 1640, 10% heat inactivated FCS, 2 mM L-glutamine, penicillin/streptomycin) and 5x$10^5$ responder cells incubated with 1x$10^5$ stimulator cells (C3H spleen cells, 2000 rad irradiated) in triplicate in round bottom 96 well plates (final volume 200 μl), and incubated with the indicated concentration of peptide (0.01, 0.1, 1, 10, 100 and 1000 μM peptide) for 5 days at 37° C., 5% $CO_2$. 1 μCi/WELL OF [$^3$H] TdR was added 12 hours before thymidine incorporation was measured. Labelled DNA from cells was harvested onto glass fiber filters with a PHD cell harvester (Cambridge, Mass.), and CPM determined by liquid scintillation counting with the use of a 1209 Rackbeta (LKB, Piscataway, N.J.).

Example 5

EAE inhibition in vivo

The finding of an effect of the human C–C' loop peptide analogs in the murine MLR assays suggested that these peptides might also be active in vivo in mice. The C–C' loop peptides were initially tested for efficacy in the SJL EAE model. In untreated animals, a high incidence of disease was observed 15–22 days after two s.c. inoculations of 1 mg of crude murine spinal cord homogenate in complete Freund's adjuvant. The severity of the disease was scored daily using the established 0–5 scale that describes the level of ascending paresis, Korngold, R., et al., 1986, Immunogenetics 24:309–315. The level of the mean EAE severity grade of mice for the untreated control group reached a maximum of 2.0. As shown in FIG. 2, the maximum severity levels reached with the groups that were given the hexapeptide CNSNQIC (SEQ ID NO:45), in either linear or the C–C' cyclic form, on day 12 (0.5 mg i.v.) was 1.0. Also shown are the results of groups of mice that received the rD-mPGPtide, a mimic of residues 86–104 of murine homolog of CD4, which was described in Jameson et al. 1994, Nature 368:744–746.

Example 6

Effect of CD4 peptide analogues on MLR proliferation of Human Peripheral Blood Lymphocytes MLR assays were carried out following the method of McDonnell et al., 1992, J. Immunol. 149:1626–1630, which is incorporated by reference in its entirety. The results of two to four independent experiments are presented in FIG. 3. The anti-CD4 antibody strongly inhibited MLR proliferation of $CD4^+$ T cell and was used as a positive control to ensure that the observed inhibition of the peptides was CD4 dependent. Peptides were synthesized with a model 430A Applied Biosystems peptide synthesizer using Fmoc chemistry. They were purified by preparative reversed-phase HPLC and homogeneity of each peptide confirmed by analytical reversed-phase HPLC. Characterization was performed by using matrix-assisted laser-desorption mass spectrometry (MALD-MS, LDI-1700 , Biomolecular Separations, Ltd., Nev.). The sequences of the synthesized peptides are as follows: D1–FG: CEVEDQKEEVQLLVFGLTC (SEQ ID NO:46); D1–CC': KNSNQIK (SEQ ID NO:4) ; D2–FG: VLQNQKKV (SEQ ID NO:47); D2–CC': RSPRGKNI .SEQ ID NO:48); D3–FG: LEAKTGKL (SEQ ID NO:49); D3–CC': WQAERASSSKS (SEQ ID NO:50); D4–FG: LSDSGQVL (SEQ ID NO:51); D4–CC': KLENKEA (SEQ ID NO:5); D4–CC'scr (scrambled): AENKKEL (SEQ ID NO:52).

Example 7

Inhibition of CD4/MHC, Class II, Interactions

The cyclic peptide CNSNQIC (SEQ ID NO:45) at 200 μM was tested to determine if the peptide inhibited the interaction of CD4 and MHC, class II. The test was performed by rosetting Raji cells and CD4-transiently transfected COS-7 cells. See: Moebius, U. et al., 1992, Proc. Natl. Acad. Sci. 89:12008–12; Moebius, U., et al., 1993, Proc. Natl. Acad. Sci. 90:8259–63. In three independent assays inhibition of 57%, 63% and 51% of the rosettes was observed.

The sequence of human CD4 cDNA is given in Maddon, P.J. et al., 1985, CELL 42:93–104, which sequence is hereby incorporated by reference. Maddon et al. refers to human CD4 as "T4." The plasmid T4-pMV7, containing the human CD4 cDNA is available from the AIDS Research and Reference Reagent Program, Division of AIDS, NIAID, NIH (McKesson BioServices, Rockville, Md.). The 3.0 Kb Eco R1 fragment of T4-pMV7 contains the 1.5 Kb CD4 cDNA.

For transfection of COS-7 cells, a CD4-expression plasmid T4-pcDNA3, was constructed by subcloning the 3.0 Kb Eco R1 fragment of T4-pMV7 into the EcoRI site of the mammalian expression vector pcDNA3 (INVITROGEN). Transfection was accomplished by DOSPER liposomal transfection reagent (BOEHRINGER MANNHEIM), by the following modification of the manufacturer's protocol.

1. In a six-well or 35mm tissue culture plate, seed ~$5\times10^4$ cells per well in 2 ml DEME containing 10% FCS (fetal calf sera, GIBCO) and nonessential amino acids.
2. Incubate the cells at 37° C., 5% $CO_2$ in a cell culture incubate until the cells are 70–80% confluent. This usually takes 18–24 h.
3. Prepare a DOSPER/DNA mixture:

Solution A: dilute 2ug T4 -pcDNA3 recombinant plasmid DNA with 20mM HBS (Hepes-buffered saline, GIBCO) to a final volume of 50ul.

Solution B: dilute 6ul DOSPER with 20 mM HBS to a final volume of 50ul. Combine solution A and B, mix gently and incubate at room temperature for 15~30min to allow the DOSPER/DNA complex to form.
4. On the day of transfection, replace the culture medium shortly before adding the DOSPER/DNA mixture with 1ml serum-free DMEM.
5. Without removing the culture medium previously added, dropwise add 100 ul of the DOSPER/DNA complex to the cultures. It was essential to add the DOSPER/DNA complex dropwise. To ensure uniform distribution, mix by gently rocking the culture plate.
6. Incubate for 6 h at 37° C., 5% $CO_2$ in a cell culture incubator.
7. Following incubation, add 1 ml DMEM with 20% FCS without removing the transfection mixture.
8. Replace the medium containing DOSPER/DNA mixture 24 h after transfection with 2ml fresh DEME with 10% FCS.
9. Determine the CD4 expression levels as a measure of transfection efficiency by flow cytometry analysis. Usually between 30% and 40% of transfected COS-7 cells expressed human CD4 as defined by immunofluorescence binding assay for the interaction between CD4 and MHC, class II, proteins in the presence of organic chemicals by rosette formation: Raji B cells $10^7$in 1 ml of RPMI medium with 10% FCS and 200 mM glutamine were added to each well 48 h post-transfection and incubated with transfected COS-7 cells in the presence of the test peptide (individually 200 uM) at 37° C. for 1 h. Following incubation, wells were washed five or six times by dropping RPMI medium with FCS into wells. Rosette formation between Raji cells and transfected COS-7 cells was scored microscopically at 100-fold magnification. The number of rosette containing more than five Raji cells was counted in 10 random optical fields in each individual well; 300–400 rosettes per well were counted as the positive rosette for rosette formation without any inhibition in the absence of any chemicals. The inhibition activity for rosette formation for each chemical was determined by the ratio of the number of rosettes obtained in the presence of this chemical to the number of rosettes in the positive control. COS-7 cells transfected with pcDNA3 vector alone served as negative controls for rosette formation. No rosettes should be observed in the negative control wells.

In a second construct, the T4-pMV7 plasmid, which contains a Tn5 neo selectable marker, was introduced into Cos-1 cells by electroporation. Stably transfected cells were isolated by selection with G-418 and the resultant transformants expressed CD4.

Raji cells were labelled with $Cr^{51}$ and rosetted to the stably T4-pMV7-transfected COS-1 cells. The addition of 200 μM of CNSNQIC (SEQ ID NO:45) caused greater than 75% inhibition of rosetting by this technique.

We claim:

1. A method of suppressing a human CD4-dependent T-cell mediated immune response comprising administering to a subject having a medical condition that is ameliorated by the suppression of a CD4-dependent T-cell mediated immune response, a therapeutically effective amount of a peptide having an amino acid sequence according to the formula:

$$N(H)(R')—X'Z'A_1A_2A_3A_4A_5Z''X''—CO—R''$$

in which:

a) N(H)(R') is the amino terminal, wherein R' is acetyl or hydrogen; and CO—R" is the carboxyl terminal, wherein R" is $NH_2$ or OH;

b) $A_1$, $A_2$, $A_3$, $A_4$ and $A_5$ are chosen according to the following scheme:

$A_1$ is N, Q or D;$A_2$ is S, T, D or N; $A_3$ is N, D, E or Q; $A_4$ is Q, N, E or M; and $A_5$ is I, L, V or A; wherein the single letters refer to L-amino acids in the single letter code;

c) X' is present or absent, and, if present, is an L-amino acid or a di- or tripeptide of D or L-amino acids selected from the group consisting of Y, W, and F, provided that no amino acid is selected more than once;

d) X" is present or absent, and if present, is a D or L-amino acid selected from the group consisting of Y, W, F, I, L or a dipeptide of D or L-amino acids selected from the group consisting of L and I; and e) Z' and Z" are amino acids that are linked to each other so the peptide is a cyclic peptide.

2. A method of suppressing a human, CD4-dependent T-cell mediated immune response comprising administering to a subject having a medical condition that is ameliorated by the suppression of a CD4-dependent T-cell mediated immune response, a therapeutically effective amount of a peptide having an amino acid sequence of:

N(H)(R')—X' Z' (CORE PEPTIDE) Z" X"—CO—R"

in which:

a) N(H)(R') is the amino terminal, wherein R' is acetyl or hydrogen; and CO–R" is the carboxyl terminal, wherein R" is NH2 or OH;

b) X' is present or absent, and, if present, is an L-amino acid or a di- or tripeptide of D or L-amino acids selected from the group consisting of Y, W, and F, provided that no amino acid is selected more than once;

c) X" is present or absent, and if present, is an L-amino acid selected from the group of consisting of Y, W, F, I, L or a dipeptide of D or L-amino acids selected from the group consisting of L and I;

d) Z' and Z" are amino acids that are linked to each other so that the peptide is a cyclic peptide; and e) the CORE PEPTIDE is selected from the group of peptides consisting of *-N-S-N-Q-L-+ (SEQ ID NO:16), *-N-S-N-Q-L-I-+(SEQ ID NO:17), *-N-S-N-Q-L-I-K-+(SEQ ID NO:18), *-N-S-N-Q-I-K-+(SEQ ID NO:4), *-N-S-N-Q-I-+(SEQ ID NO:1) *-K-N-S-N-Q-L-+(SEQ ID NO:22), *-K-N-S-N-Q-L-I-+(SEQ ID NO:23), *-K-N-S-N-Q-L-I-K-+(SEQ ID NO:2) *-K-N-S-N-Q-I-+(SEQ ID NO:3) and *-K-N-S-N-Q-I-K-+ (SEQ ID NO:4), wherein * and + designate the amino and carboxyl termini, respectively, and the single letters designate L-amino acids according to the single letter code or wherein * and + designate the amino and carboxyl termini, respectively and the single letters designate D-amino acids according to the single letter code.

3. The method of claim 2, wherein the peptide, at a concentration of at most 200 $\mu$M:

a) causes less than a 20% decrease in lipopolysaccharide-stimulated proliferation of human peripheral blood lymphocytes in vitro; and b) inhibits greater than 25% of activated T-cell proliferation in an in vitro human mixed lymphocyte reaction.

4. The method of claim 2, wherein the medical condition is related to an allograft.

5. The method of claim 2, wherein the CORE PEPTIDE is selected from the group consisting of *-K-N-S-N-Q-L-I-K-+(SEQ ID NO:2), *-K-N-S-N-Q-I-K-+(SEQ ID NO:4), *-N-S-N-Q-L-I-+(SEQ ID NO:17), and *-N-S-N-Q-I-+ (SEQ ID NO:1), wherein * and + designate the amino and carboxyl termini, respectively, and the single letters designate L-amino acids according to the single letter code, or wherein * and + designate the carboxyl and amino termini, respectively and the single letters designate D-amino acids according to the single letter code.

6. The method of claim 2, wherein the CORE PEPTIDE is *-N-S-N-Q-I-+ (SEQ ID NO:1) and, wherein * and + designate the amino and carboxyl termini, respectively, and the single letters designate L-amino acids according to the single letter code.

7. The method of claim 6, wherein the peptide is CNSNQIC (SEQ ID NO:45).

8. The method of claim 6, wherein the peptide is YCNSNQIC (SEQ ID NO: 53).

9. The method of claim 1, wherein the peptide, at a concentration of at most 200 $\mu$M:

a) causes less than a 20% decrease in lipopolysaccharide-stimulated proliferation of human peripheral blood lymphocytes in vitro; and b) inhibits greater than 25% of activated T-cell proliferation in an in vitro human mixed lymphocyte reaction.

10. The method of claim 1, wherein the medical condition is related to an allograft.

11. The method of claim 1 or claim 2, wherein the medical condition is multiple sclerosis.

* * * * *

SEQUENCE LISTING ( 1 ) GENERAL INFORMATION:

( i i i ) NUMBER OF SEQUENCES: 53

( 2 ) INFORMATION FOR SEQ ID NO:1:

( i ) SEQUENCE CHARACTERISTICS:
( A ) LENGTH: 5 amino acids
( B ) TYPE: amino acid
( C ) STRANDEDNESS:
( D ) TOPOLOGY: unknown ( i i ) MOLECULE TYPE: peptide ( x i ) SEQUENCE DESCRIPTION: SEQ ID NO:1:

Asn Ser Asn Gln Ile
1 5

( 2 ) INFORMATION FOR SEQ ID NO:2:

( i ) SEQUENCE CHARACTERISTICS:
( A ) LENGTH: 6 amino acids
( B ) TYPE: amino acid
( C ) STRANDEDNESS:
( D ) TOPOLOGY: unknown ( i i ) MOLECULE TYPE: peptide ( x i ) SEQUENCE DESCRIPTION: SEQ ID NO:2:

Lys Asn Ser Asn Gln Ile
1 5

( 2 ) INFORMATION FOR SEQ ID NO:3:

( i ) SEQUENCE CHARACTERISTICS:
( A ) LENGTH: 8 amino acids
( B ) TYPE: amino acid
( C ) STRANDEDNESS:
( D ) TOPOLOGY: unknown ( i i ) MOLECULE TYPE: peptide ( x i ) SEQUENCE DESCRIPTION: SEQ ID NO:3:

Lys Asn Ser Asn Gln Leu Ile Lys
1 5

( 2 ) INFORMATION FOR SEQ ID NO:4:

( i ) SEQUENCE CHARACTERISTICS:
( A ) LENGTH: 7 amino acids
( B ) TYPE: amino acid
( C ) STRANDEDNESS:
( D ) TOPOLOGY: unknown ( i i ) MOLECULE TYPE: peptide ( x i ) SEQUENCE DESCRIPTION: SEQ ID NO:4:

Lys Asn Ser Asn Gln Ile Lys
1 5

( 2 ) INFORMATION FOR SEQ ID NO:5:

( i ) SEQUENCE CHARACTERISTICS:
( A ) LENGTH: 7 amino acids
( B ) TYPE: amino acid
( C ) STRANDEDNESS:
( D ) TOPOLOGY: unknown ( i i ) MOLECULE TYPE: peptide ( x i ) SEQUENCE DESCRIPTION: SEQ ID NO:5:

Lys Leu Glu Asn Lys Glu Ala
1 5

( 2 ) INFORMATION FOR SEQ ID NO:6:

( i ) SEQUENCE CHARACTERISTICS:
( A ) LENGTH: 8 amino acids
( B ) TYPE: amino acid
( C ) STRANDEDNESS:
( D ) TOPOLOGY: unknown ( i i ) MOLECULE TYPE: peptide ( x i ) SEQUENCE DESCRIPTION: SEQ ID NO:6:

Leu Ser Asp Ser Gly Gln Val Leu
1 5

( 2 ) INFORMATION FOR SEQ ID NO:7:

( i ) SEQUENCE CHARACTERISTICS:
( A ) LENGTH: 4 amino acids
( B ) TYPE: amino acid
( C ) STRANDEDNESS:
( D ) TOPOLOGY: unknown ( i i ) MOLECULE TYPE: peptide ( x i ) SEQUENCE DESCRIPTION: SEQ ID NO:7:

Asn Gln Leu Ile
1

( 2 ) INFORMATION FOR SEQ ID NO:8:

( i ) SEQUENCE CHARACTERISTICS:
( A ) LENGTH: 5 amino acids
( B ) TYPE: amino acid
( C ) STRANDEDNESS:
( D ) TOPOLOGY: unknown ( i i ) MOLECULE TYPE: peptide ( x i ) SEQUENCE DESCRIPTION: SEQ ID NO:8:

Asn Gln Leu Ile Lys
1 5

( 2 ) INFORMATION FOR SEQ ID NO:9:

( i ) SEQUENCE CHARACTERISTICS:
( A ) LENGTH: 4 amino acids
( B ) TYPE: amino acid
( C ) STRANDEDNESS:
( D ) TOPOLOGY: unknown ( i i ) MOLECULE TYPE: peptide ( x i ) SEQUENCE DESCRIPTION: SEQ ID NO:9:

Asn Gln Ile Lys
1

( 2 ) INFORMATION FOR SEQ ID NO:10:

( i ) SEQUENCE CHARACTERISTICS:
( A ) LENGTH: 4 amino acids
( B ) TYPE: amino acid
( C ) STRANDEDNESS:
( D ) TOPOLOGY: unknown ( i i ) MOLECULE TYPE: peptide ( x i ) SEQUENCE DESCRIPTION: SEQ ID NO:10:

Ser Asn Gln Leu
1

( 2 ) INFORMATION FOR SEQ ID NO:11:

( i ) SEQUENCE CHARACTERISTICS:
( A ) LENGTH: 5 amino acids
( B ) TYPE: amino acid
( C ) STRANDEDNESS:
( D ) TOPOLOGY: unknown ( i i ) MOLECULE TYPE: peptide ( x i ) SEQUENCE DESCRIPTION: SEQ ID NO:11:

Ser Asn Gln Leu Ile
1 5

( 2 ) INFORMATION FOR SEQ ID NO:12:

( i ) SEQUENCE CHARACTERISTICS:
( A ) LENGTH: 6 amino acids
( B ) TYPE: amino acid
( C ) STRANDEDNESS:
( D ) TOPOLOGY: unknown ( i i ) MOLECULE TYPE: peptide ( x i ) SEQUENCE DESCRIPTION: SEQ ID NO:12:

Ser Asn Gln Leu Ile Lys
1 5

( 2 ) INFORMATION FOR SEQ ID NO:13:

( i ) SEQUENCE CHARACTERISTICS:
( A ) LENGTH: 4 amino acids
( B ) TYPE: amino acid
( C ) STRANDEDNESS:
( D ) TOPOLOGY: unknown ( i i ) MOLECULE TYPE: peptide ( x i ) SEQUENCE DESCRIPTION: SEQ ID NO:13:

Ser Asn Gln Ile
1

( 2 ) INFORMATION FOR SEQ ID NO:14:

( i ) SEQUENCE CHARACTERISTICS:
( A ) LENGTH: 5 amino acids
( B ) TYPE: amino acid
( C ) STRANDEDNESS:
( D ) TOPOLOGY: unknown ( i i ) MOLECULE TYPE: peptide ( x i ) SEQUENCE DESCRIPTION: SEQ ID NO:14:

Ser Asn Gln Ile Lys
1 5

( 2 ) INFORMATION FOR SEQ ID NO:15:

( i ) SEQUENCE CHARACTERISTICS:
( A ) LENGTH: 4 amino acids
( B ) TYPE: amino acid
( C ) STRANDEDNESS:
( D ) TOPOLOGY: unknown ( i i ) MOLECULE TYPE: peptide ( x i ) SEQUENCE DESCRIPTION: SEQ ID NO:15:

Asn Ser Asn Gln
1

( 2 ) INFORMATION FOR SEQ ID NO:16:

( i ) SEQUENCE CHARACTERISTICS:
( A ) LENGTH: 5 amino acids
( B ) TYPE: amino acid
( C ) STRANDEDNESS:
( D ) TOPOLOGY: unknown ( i i ) MOLECULE TYPE: peptide ( x i ) SEQUENCE DESCRIPTION: SEQ ID NO:16:

-continued

Asn Ser Asn Gln Leu
1 5

( 2 ) INFORMATION FOR SEQ ID NO:17:

( i ) SEQUENCE CHARACTERISTICS:
( A ) LENGTH: 6 amino acids
( B ) TYPE: amino acid
( C ) STRANDEDNESS:
( D ) TOPOLOGY: unknown ( i i ) MOLECULE TYPE: peptide ( x i ) SEQUENCE DESCRIPTION: SEQ ID NO:17:

Asn Ser Asn Gln Leu Ile
1 5

( 2 ) INFORMATION FOR SEQ ID NO:18:

( i ) SEQUENCE CHARACTERISTICS:
( A ) LENGTH: 7 amino acids
( B ) TYPE: amino acid
( C ) STRANDEDNESS:
( D ) TOPOLOGY: unknown ( i i ) MOLECULE TYPE: peptide ( x i ) SEQUENCE DESCRIPTION: SEQ ID NO:18:

Asn Ser Asn Gln Leu Ile Lys
1 5

( 2 ) INFORMATION FOR SEQ ID NO:19:

( i ) SEQUENCE CHARACTERISTICS:
( A ) LENGTH: 6 amino acids
( B ) TYPE: amino acid
( C ) STRANDEDNESS:
( D ) TOPOLOGY: unknown ( i i ) MOLECULE TYPE: peptide ( x i ) SEQUENCE DESCRIPTION: SEQ ID NO:19:

Asn Ser Asn Gln Ile Lys
1 5

( 2 ) INFORMATION FOR SEQ ID NO:20:

( i ) SEQUENCE CHARACTERISTICS:
( A ) LENGTH: 4 amino acids
( B ) TYPE: amino acid
( C ) STRANDEDNESS:
( D ) TOPOLOGY: unknown ( i i ) MOLECULE TYPE: peptide ( x i ) SEQUENCE DESCRIPTION: SEQ ID NO:20:

Lys Asn Ser Asn
1

( 2 ) INFORMATION FOR SEQ ID NO:21:

( i ) SEQUENCE CHARACTERISTICS:
( A ) LENGTH: 5 amino acids
( B ) TYPE: amino acid
( C ) STRANDEDNESS:
( D ) TOPOLOGY: unknown ( i i ) MOLECULE TYPE: peptide ( x i ) SEQUENCE DESCRIPTION: SEQ ID NO:21:

Lys Asn Ser Asn Gln
1 5

( 2 ) INFORMATION FOR SEQ ID NO:22:

( i ) SEQUENCE CHARACTERISTICS:
( A ) LENGTH: 6 amino acids
( B ) TYPE: amino acid
( C ) STRANDEDNESS:
( D ) TOPOLOGY: unknown ( i i ) MOLECULE TYPE: peptide ( x i ) SEQUENCE DESCRIPTION: SEQ ID NO:22:

Lys Asn Ser Asn Gln Leu
1 5

( 2 ) INFORMATION FOR SEQ ID NO:23:

( i ) SEQUENCE CHARACTERISTICS:
( A ) LENGTH: 7 amino acids
( B ) TYPE: amino acid
( C ) STRANDEDNESS:
( D ) TOPOLOGY: unknown ( i i ) MOLECULE TYPE: peptide ( x i ) SEQUENCE DESCRIPTION: SEQ ID NO:23:

Lys Asn Ser Asn Gln Leu Ile
1 5

( 2 ) INFORMATION FOR SEQ ID NO:24:

( i ) SEQUENCE CHARACTERISTICS:
( A ) LENGTH: 4 amino acids
( B ) TYPE: amino acid
( C ) STRANDEDNESS:
( D ) TOPOLOGY: unknown ( i i ) MOLECULE TYPE: peptide ( x i ) SEQUENCE DESCRIPTION: SEQ ID NO:24:

Glu Asn Lys Glu
1

( 2 ) INFORMATION FOR SEQ ID NO:25:

( i ) SEQUENCE CHARACTERISTICS:
( A ) LENGTH: 5 amino acids
( B ) TYPE: amino acid
( C ) STRANDEDNESS:
( D ) TOPOLOGY: unknown ( i i ) MOLECULE TYPE: peptide ( x i ) SEQUENCE DESCRIPTION: SEQ ID NO:25:

Glu Asn Lys Glu Ala
1 5

( 2 ) INFORMATION FOR SEQ ID NO:26:

( i ) SEQUENCE CHARACTERISTICS:
( A ) LENGTH: 4 amino acids
( B ) TYPE: amino acid
( C ) STRANDEDNESS:
( D ) TOPOLOGY: unknown ( i i ) MOLECULE TYPE: peptide ( x i ) SEQUENCE DESCRIPTION: SEQ ID NO:26:

Leu Glu Asn Lys
1

( 2 ) INFORMATION FOR SEQ ID NO:27:

( i ) SEQUENCE CHARACTERISTICS:
( A ) LENGTH: 5 amino acids
( B ) TYPE: amino acid
( C ) STRANDEDNESS:
( D ) TOPOLOGY: unknown ( i i ) MOLECULE TYPE: peptide ( x i ) SEQUENCE DESCRIPTION: SEQ ID NO:27:

Leu Glu Asn Lys Glu
1 5

( 2 ) INFORMATION FOR SEQ ID NO:28:

( i ) SEQUENCE CHARACTERISTICS:
( A ) LENGTH: 6 amino acids
( B ) TYPE: amino acid
( C ) STRANDEDNESS:
( D ) TOPOLOGY: unknown ( i i ) MOLECULE TYPE: peptide ( x i ) SEQUENCE DESCRIPTION: SEQ ID NO:28:

Leu Glu Asn Lys Glu Ala
1 5

( 2 ) INFORMATION FOR SEQ ID NO:29:

( i ) SEQUENCE CHARACTERISTICS:
( A ) LENGTH: 5 amino acids
( B ) TYPE: amino acid
( C ) STRANDEDNESS:
( D ) TOPOLOGY: unknown ( i i ) MOLECULE TYPE: peptide ( x i ) SEQUENCE DESCRIPTION: SEQ ID NO:29:

Lys Leu Glu Asn Lys
1 5

( 2 ) INFORMATION FOR SEQ ID NO:30:

( i ) SEQUENCE CHARACTERISTICS:
( A ) LENGTH: 6 amino acids
( B ) TYPE: amino acid
( C ) STRANDEDNESS:
( D ) TOPOLOGY: unknown ( i i ) MOLECULE TYPE: peptide ( x i ) SEQUENCE DESCRIPTION: SEQ ID NO:30:

Lys Leu Glu Asn Lys Glu
1 5

( 2 ) INFORMATION FOR SEQ ID NO:31:

( i ) SEQUENCE CHARACTERISTICS:
( A ) LENGTH: 4 amino acids
( B ) TYPE: amino acid
( C ) STRANDEDNESS:
( D ) TOPOLOGY: unknown ( i i ) MOLECULE TYPE: peptide ( x i ) SEQUENCE DESCRIPTION: SEQ ID NO:31:

Ser Gly Gln Val
1

( 2 ) INFORMATION FOR SEQ ID NO:32:

( i ) SEQUENCE CHARACTERISTICS:
( A ) LENGTH: 5 amino acids
( B ) TYPE: amino acid
( C ) STRANDEDNESS:
( D ) TOPOLOGY: unknown ( i i ) MOLECULE TYPE: peptide ( x i ) SEQUENCE DESCRIPTION: SEQ ID NO:32:

Ser Gly Gln Val Leu
1 5

( 2 ) INFORMATION FOR SEQ ID NO:33:

( i ) SEQUENCE CHARACTERISTICS:
( A ) LENGTH: 4 amino acids
( B ) TYPE: amino acid
( C ) STRANDEDNESS:
( D ) TOPOLOGY: unknown ( i i ) MOLECULE TYPE: peptide ( x i ) SEQUENCE DESCRIPTION: SEQ ID NO:33:

Asp Ser Gly Gln
1

( 2 ) INFORMATION FOR SEQ ID NO:34:

( i ) SEQUENCE CHARACTERISTICS:
( A ) LENGTH: 5 amino acids
( B ) TYPE: amino acid
( C ) STRANDEDNESS:
( D ) TOPOLOGY: unknown ( i i ) MOLECULE TYPE: peptide ( x i ) SEQUENCE DESCRIPTION: SEQ ID NO:34:

Asp Ser Gly Gln Val
1 5

( 2 ) INFORMATION FOR SEQ ID NO:35:

( i ) SEQUENCE CHARACTERISTICS:
( A ) LENGTH: 6 amino acids
( B ) TYPE: amino acid
( C ) STRANDEDNESS:
( D ) TOPOLOGY: unknown ( i i ) MOLECULE TYPE: peptide ( x i ) SEQUENCE DESCRIPTION: SEQ ID NO:35:

Asp Ser Gly Gln Val Leu
1 5

( 2 ) INFORMATION FOR SEQ ID NO:36:

( i ) SEQUENCE CHARACTERISTICS:
( A ) LENGTH: 5 amino acids
( B ) TYPE: amino acid
( C ) STRANDEDNESS:
( D ) TOPOLOGY: unknown ( i i ) MOLECULE TYPE: peptide ( x i ) SEQUENCE DESCRIPTION: SEQ ID NO:36:

Ser Asp Ser Gly Gln
1 5

(2) INFORMATION FOR SEQ ID NO:37:

(i) SEQUENCE CHARACTERISTICS:
(A) LENGTH: 6 amino acids
(B) TYPE: amino acid
(C) STRANDEDNESS:
(D) TOPOLOGY: unknown (ii) MOLECULE TYPE: peptide (xi) SEQUENCE DESCRIPTION: SEQ ID NO:37:

Ser Asp Ser Gly Gln Val
1 5

(2) INFORMATION FOR SEQ ID NO:38:

(i) SEQUENCE CHARACTERISTICS:
(A) LENGTH: 7 amino acids
(B) TYPE: amino acid
(C) STRANDEDNESS:
(D) TOPOLOGY: unknown (ii) MOLECULE TYPE: peptide (xi) SEQUENCE DESCRIPTION: SEQ ID NO:38:

Ser Asp Ser Gly Gln Val Leu
1 5

(2) INFORMATION FOR SEQ ID NO:39:

(i) SEQUENCE CHARACTERISTICS:
(A) LENGTH: 6 amino acids
(B) TYPE: amino acid
(C) STRANDEDNESS:
(D) TOPOLOGY: unknown (ii) MOLECULE TYPE: peptide (xi) SEQUENCE DESCRIPTION: SEQ ID NO:39:

Leu Ser Asp Ser Gly Gln
1 5

(2) INFORMATION FOR SEQ ID NO:40:

(i) SEQUENCE CHARACTERISTICS:
(A) LENGTH: 7 amino acids
(B) TYPE: amino acid
(C) STRANDEDNESS:
(D) TOPOLOGY: unknown (ii) MOLECULE TYPE: peptide (xi) SEQUENCE DESCRIPTION: SEQ ID NO:40:

Leu Ser Asp Ser Gly Gln Val
1 5

(2) INFORMATION FOR SEQ ID NO:41:

(i) SEQUENCE CHARACTERISTICS:
(A) LENGTH: 5 amino acids
(B) TYPE: amino acid
(C) STRANDEDNESS:
(D) TOPOLOGY: unknown (ii) MOLECULE TYPE: peptide (xi) SEQUENCE DESCRIPTION: SEQ ID NO:41:

Ile Gln Asn Ser Asn
1 5

( 2 ) INFORMATION FOR SEQ ID NO:42:

( i ) SEQUENCE CHARACTERISTICS:
( A ) LENGTH: 7 amino acids
( B ) TYPE: amino acid
( C ) STRANDEDNESS:
( D ) TOPOLOGY: unknown ( i i ) MOLECULE TYPE: peptide ( x i ) SEQUENCE DESCRIPTION: SEQ ID NO:42:

Lys Ile Gln Asn Ser Asn Lys
1 5

( 2 ) INFORMATION FOR SEQ ID NO:43:

( i ) SEQUENCE CHARACTERISTICS:
( A ) LENGTH: 7 amino acids
( B ) TYPE: amino acid
( C ) STRANDEDNESS:
( D ) TOPOLOGY: unknown ( i i ) MOLECULE TYPE: peptide ( x i ) SEQUENCE DESCRIPTION: SEQ ID NO:43:

Lys Ile Leu Gln Ser Asn Lys
1 5

( 2 ) INFORMATION FOR SEQ ID NO:44:

( i ) SEQUENCE CHARACTERISTICS:
( A ) LENGTH: 7 amino acids
( B ) TYPE: amino acid
( C ) STRANDEDNESS:
( D ) TOPOLOGY: linear ( i i ) MOLECULE TYPE: peptide ( x i ) SEQUENCE DESCRIPTION: SEQ ID NO:44:

Cys Asn Ser Asn Gln Ile Cys
1 5

( 2 ) INFORMATION FOR SEQ ID NO:45:

( i ) SEQUENCE CHARACTERISTICS:
( A ) LENGTH: 7 amino acids
( B ) TYPE: amino acid
( C ) STRANDEDNESS:
( D ) TOPOLOGY: circular ( i i ) MOLECULE TYPE: peptide ( x i ) SEQUENCE DESCRIPTION: SEQ ID NO:45:

Cys Asn Ser Asn Gln Ile Cys
1 5

( 2 ) INFORMATION FOR SEQ ID NO:46:

( i ) SEQUENCE CHARACTERISTICS:
( A ) LENGTH: 19 amino acids
( B ) TYPE: amino acid
( C ) STRANDEDNESS:
( D ) TOPOLOGY: unknown ( i i ) MOLECULE TYPE: peptide ( x i ) SEQUENCE DESCRIPTION: SEQ ID NO:46:

-continued

Cys Glu Val Glu Asp Gln Lys Glu Glu Val Gln Leu Leu Val Phe Gly
1 5 10 15

Leu Thr Cys ( 2 ) INFORMATION FOR SEQ ID NO:47:

( i ) SEQUENCE CHARACTERISTICS:
( A ) LENGTH: 8 amino acids
( B ) TYPE: amino acid
( C ) STRANDEDNESS:
( D ) TOPOLOGY: unknown ( i i ) MOLECULE TYPE: peptide ( x i ) SEQUENCE DESCRIPTION: SEQ ID NO:47:

Val Leu Gln Asn Gln Lys Lys Val
1 5

( 2 ) INFORMATION FOR SEQ ID NO:48:

( i ) SEQUENCE CHARACTERISTICS:
( A ) LENGTH: 8 amino acids
( B ) TYPE: amino acid
( C ) STRANDEDNESS:
( D ) TOPOLOGY: unknown ( i i ) MOLECULE TYPE: peptide ( x i ) SEQUENCE DESCRIPTION: SEQ ID NO:48:

Arg Ser Pro Arg Gly Lys Asn Ile
1 5

( 2 ) INFORMATION FOR SEQ ID NO:49:

( i ) SEQUENCE CHARACTERISTICS:
( A ) LENGTH: 8 amino acids
( B ) TYPE: amino acid
( C ) STRANDEDNESS:
( D ) TOPOLOGY: unknown ( i i ) MOLECULE TYPE: peptide ( x i ) SEQUENCE DESCRIPTION: SEQ ID NO:49:

Leu Glu Ala Lys Thr Gly Lys Leu
1 5

( 2 ) INFORMATION FOR SEQ ID NO:50:

( i ) SEQUENCE CHARACTERISTICS:
( A ) LENGTH: 11 amino acids
( B ) TYPE: amino acid
( C ) STRANDEDNESS:
( D ) TOPOLOGY: unknown ( i i ) MOLECULE TYPE: peptide ( x i ) SEQUENCE DESCRIPTION: SEQ ID NO:50:

Trp Gln Ala Glu Arg Ala Ser Ser Ser Lys Ser
1 5 10

( 2 ) INFORMATION FOR SEQ ID NO:51:

( i ) SEQUENCE CHARACTERISTICS:
( A ) LENGTH: 8 amino acids
( B ) TYPE: amino acid
( C ) STRANDEDNESS:
( D ) TOPOLOGY: unknown ( i i ) MOLECULE TYPE: peptide -continued ( x i ) SEQUENCE DESCRIPTION: SEQ ID NO:51:

Leu Ser Asp Ser Gly Gln Val Leu
1 5

( 2 ) INFORMATION FOR SEQ ID NO:52:

( i ) SEQUENCE CHARACTERISTICS:
( A ) LENGTH: 7 amino acids
( B ) TYPE: amino acid
( C ) STRANDEDNESS:
( D ) TOPOLOGY: unknown ( i i ) MOLECULE TYPE: peptide ( x i ) SEQUENCE DESCRIPTION: SEQ ID NO:52:

Ala Glu Asn Lys Lys Glu Leu
1 5

( 2 ) INFORMATION FOR SEQ ID NO:53:

( i ) SEQUENCE CHARACTERISTICS:
( A ) LENGTH: 8 amino acids
( B ) TYPE: amino acid
( C ) STRANDEDNESS:
( D ) TOPOLOGY: circular ( i i ) MOLECULE TYPE: peptide ( x i ) SEQUENCE DESCRIPTION: SEQ ID NO:53:

Tyr Cys Asn Ser Asn Gln Ile Cys
1 5